United States Patent [19]

Ouchi

[11] Patent Number: 5,957,900
[45] Date of Patent: Sep. 28, 1999

[54] TREATMENT ACCESSORY FOR ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 08/890,359

[22] Filed: Jul. 9, 1997

[30] Foreign Application Priority Data

| Jul. 10, 1996 | [JP] | Japan | 8-180409 |
| Jul. 10, 1996 | [JP] | Japan | 8-180410 |
| Jul. 10, 1996 | [JP] | Japan | 8-180411 |
| Oct. 23, 1996 | [JP] | Japan | 8-280425 |
| Oct. 23, 1996 | [JP] | Japan | 8-280426 |
| Oct. 23, 1996 | [JP] | Japan | 8-280427 |

[51] Int. Cl.[6] .................................................. A61M 25/00
[52] U.S. Cl. ........................... 604/264; 604/104; 604/21; 600/104
[58] Field of Search .................... 604/264, 280, 604/283, 21, 52, 53, 104–107; 600/104

[56] References Cited

U.S. PATENT DOCUMENTS

| 4,178,810 | 12/1979 | Takahashi . |
| 4,393,872 | 7/1983 | Reznik et al. . |
| 4,461,283 | 7/1984 | Doi . |
| 4,485,812 | 12/1984 | Harada . |
| 4,643,720 | 2/1987 | Lanciano . |
| 4,650,466 | 3/1987 | Luther . |
| 4,655,219 | 4/1987 | Petruzzi . |
| 4,740,195 | 4/1988 | Lanciano . |
| 4,878,893 | 11/1989 | Chin . |
| 5,030,213 | 7/1991 | Rumberger . |
| 5,064,428 | 11/1991 | Cope et al. . |
| 5,397,320 | 3/1995 | Essig et al. . |
| 5,486,183 | 1/1996 | Middleman et al. . |
| 5,601,572 | 2/1997 | Middleman et al. . |
| 5,632,746 | 5/1997 | Middleman et al. . |
| 5,720,754 | 2/1998 | Middleman et al. . |
| 5,749,879 | 5/1998 | Middleman et al. . |

FOREIGN PATENT DOCUMENTS

| 61-181452 | 8/1986 | Japan . |
| 61-181456 | 8/1986 | Japan . |
| 2-4293 | 1/1990 | Japan . |
| 92/05828 | 4/1992 | WIPO . |
| 95/31149 | 11/1995 | WIPO . |

OTHER PUBLICATIONS

Gastrointestinal Endoscopy, Martin B. Grossman, M.D., *Clinical Symposia,* vol. 32, No. 3, CIBA Pharmaceutical Company, Summitt, New Jersey, 1980.

*Primary Examiner*—John D. Yasko
*Attorney, Agent, or Firm*—Greenblum & Bernstein, P.L.C.

[57] ABSTRACT

An accessory of an endoscope includes a tube. At least the distal end portion of the tube is formed to have a predetermined resilience, and a plurality of slits extending in the axial direction of the tube are formed at the distal end portion of the tube. A mechanism is provided to bias the distal end of the tube towards the proximal end thereof so that the band portions between the plurality of slits radially expand to define a plurality of openings. The mechanism can forcibly strain the band portions and forcibly and radially expand the band portions.

29 Claims, 26 Drawing Sheets

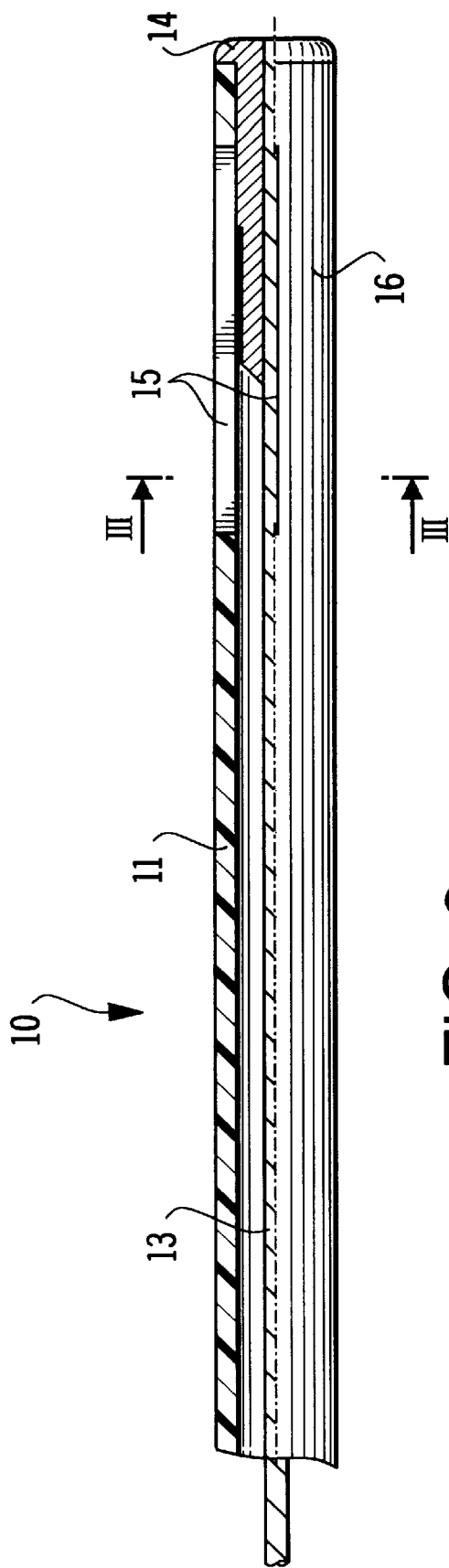
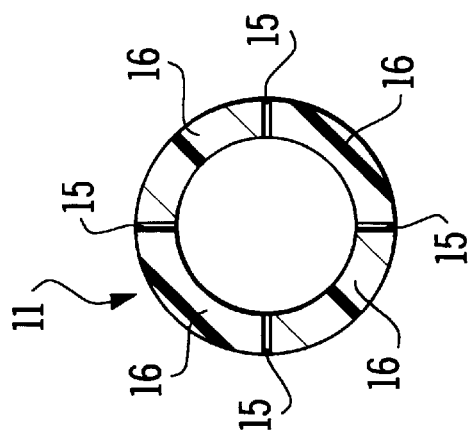
FIG. 2
FIG. 3

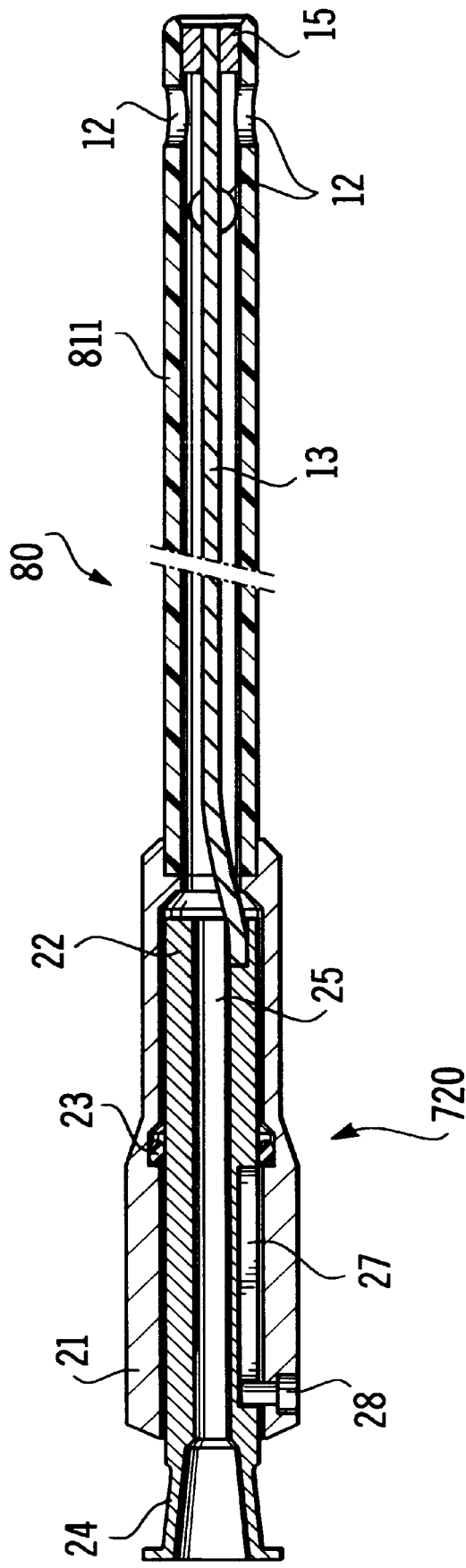
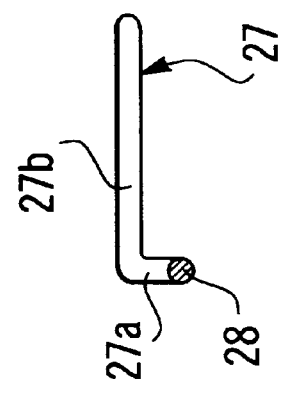
FIG. 9
FIG. 9A

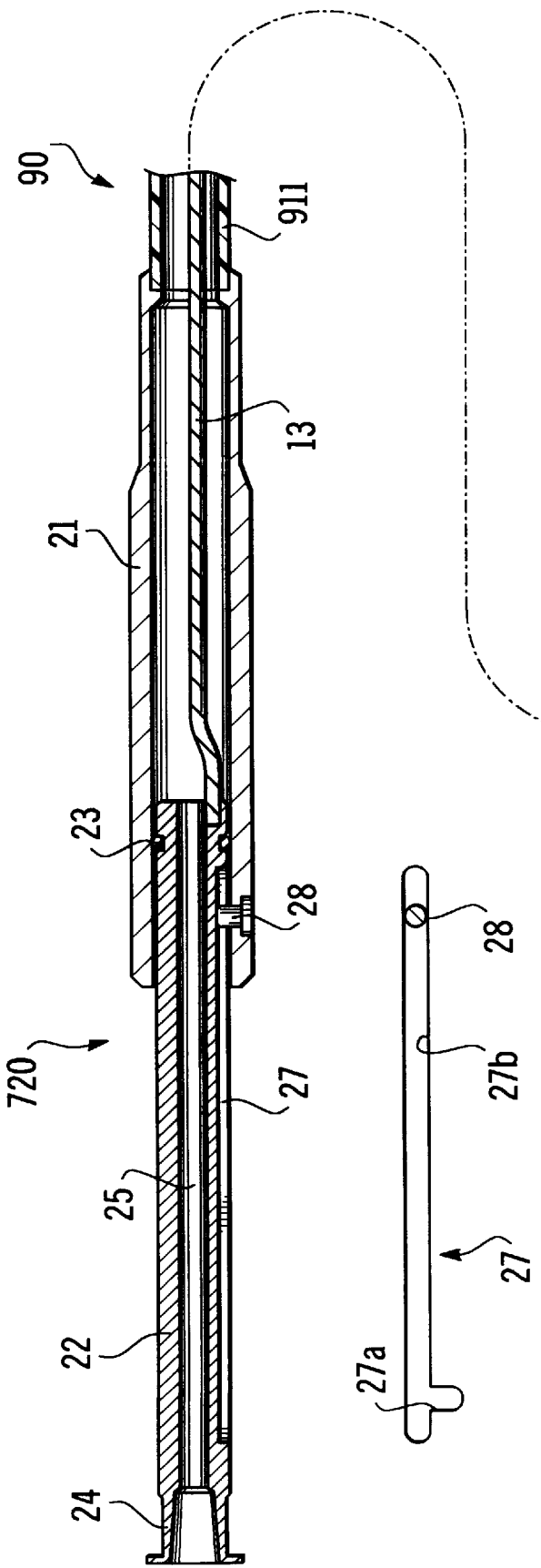
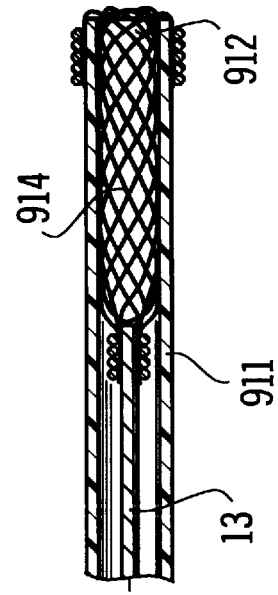
FIG. 15
FIG. 15A

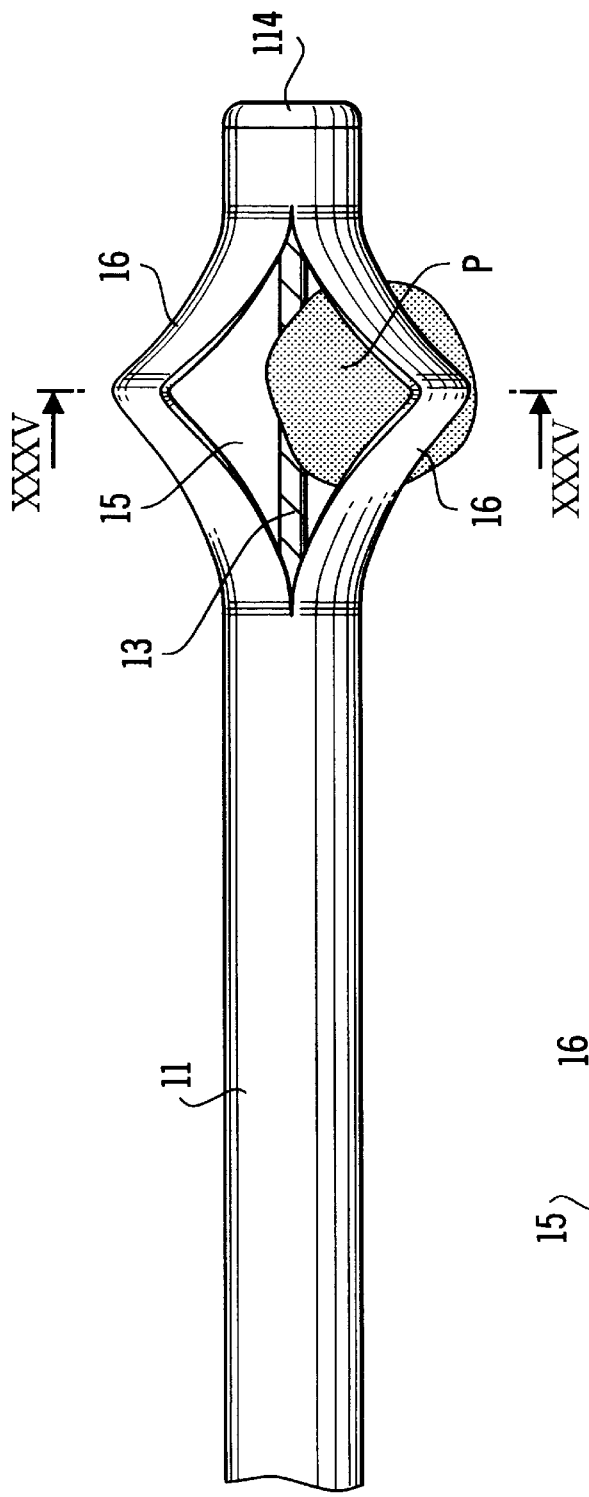
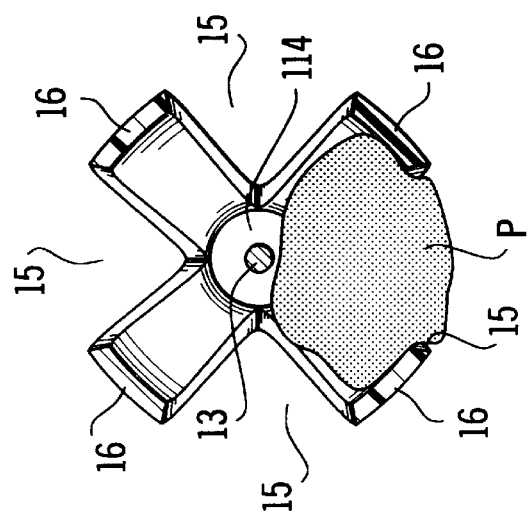

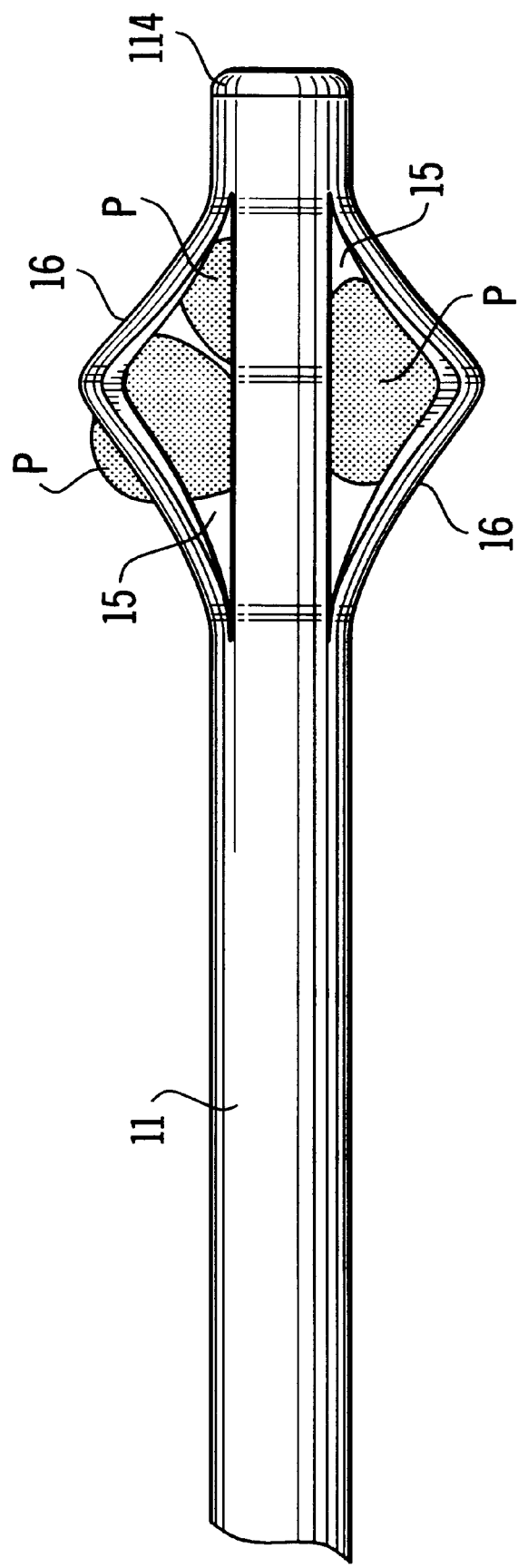

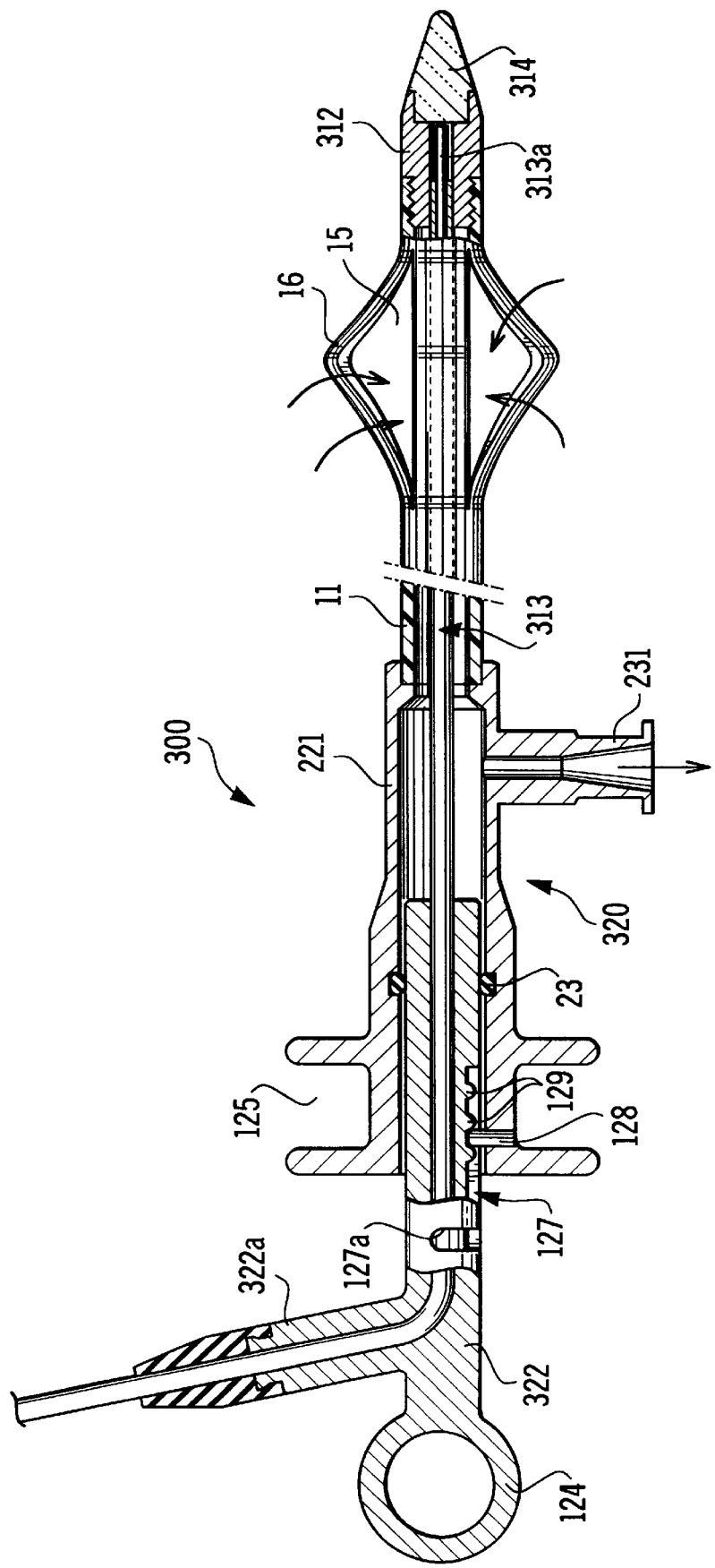
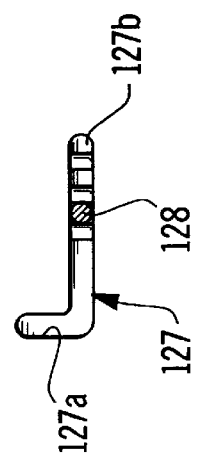
FIG. 37
FIG. 37A

5,957,900

TREATMENT ACCESSORY FOR ENDOSCOPE

BACKGROUND OF THE INVENTION

The present invention relates to a treatment accessory for an endoscope and, in particular, to a treatment accessory capable of dispensing fluids and aspirating liquids or other material.

When using an endoscope, it is usually important to ensure that the area around an affected area in a body cavity is clean and easily visible. As such, treatment accessories are provided for insertion in a channel of the endoscope which dispense liquids, such as cleaning fluid or dye, which aspirate liquids, such as the cleaning liquid, dye, blood or the like, and which collect particles such as food residue and the like.

A conventional treatment accessory for dispensing cleaning liquid is provided at a distal end thereof with a helical groove which provides a directed spray of cleaning fluid.

A conventional treatment accessory for aspiration is a flexible tube with an aspiration opening at a distal end thereof.

A conventional treatment accessory for collecting particles is provided, at a distal end thereof, with a basket-like collector which is formed from a plurality of wires. In operation, the collector is extended from a distal end of the channel and the collector expands resiliently to an open state. A particle to be collected is then positioned in the collector and the collector is drawn into the channel to capture the particle.

Generally, the dispensing treatment accessory, the aspiration treatment accessory, and the collecting treatment accessory must be used separately. That is, if the dispensing treatment accessory is used for aspiration, the helical groove may quickly become clogged with particles, such as food residue, that may be present in the liquid in the body cavity. Also, if the aspiration treatment accessory is used for dispensing, it is difficult to provide a directed spray and to provide sufficient force to adequately clean an affected area. Further, the collecting treatment accessory is generally not provided with a pathway for liquid flow.

Thus, the collecting treatment accessory must first be used to collect large particles. Then, the collecting treatment accessory is removed and the dispensing treatment accessory or the aspiration treatment accessory is inserted. Thereafter, for example, the dispensing treatment accessory is used to dispense a liquid, and the dispensing treatment accessory must be removed and replaced with the aspiration treatment accessory to aspirate the liquid.

Further, if the liquid to be aspirated still includes particles which are larger than the aspiration opening of the aspiration treatment accessory, the aspiration treatment accessory may become clogged and have to be removed and cleaned during the aspiration operation.

The conventional collecting treatment accessory has the further problem. That is, since the collector is generally made of thin wires, the resilient force generated to expand the collector after being extended from the channel of the endoscope is relatively weak and may not be sufficient to overcome the stickiness of certain kinds of mucous or the like. Also, the formation of the collector using thin wires may require specialized tools and due to the bundling of the wires to form the collector, the collector may be too large to fit into a narrow channeled endoscope.

The cleaning of an affected area is particularly important when an affected area is to be treated by cauterization or the like. Cauterization is performed to stop various kinds of internal bleeding, such as bleeding from tumorous areas of the digestive tract or bleeding caused by treatment accessories or the like. Cauterization is performed using a treatment accessory provided with a laser probe, a heat probe, a high-frequency probe, a microwave probe or the like, mounted at the end of a flexible sheath.

However, since the dispersing treatment accessory or aspiration treatment accessory must be removed before inserting the cauterization treatment accessory, additional blood may come out of the affected area such that blood adhering to the surrounding area is cauterized and coagulates rather than the affected area itself.

SUMMARY OF THE INVENTION

It is therefore an object of the present invention to provide an improved treatment accessory for an endoscope which has a simple structure and which is less likely to clog during aspiration.

It is a further object of the present invention to provide an improved treatment accessory for an endoscope which has a simple structure and which, if clogged, can be operated to remove the clogging without removal from the endoscope.

It is a further object of the present invention to provide an improved treatment accessory for an endoscope which has a simple structure and which can be used to efficiently collect particles from inside a body cavity.

It is a further object of the present invention to provide an improved treatment accessory for an endoscope which has a simple structure but which can be used for a variety of purposes, such purposes including dispensing liquids such as cleaning liquids and dyes, aspirating liquids and other materials, collecting particles, and cauterization of affected areas.

For the above objects, according to one aspect of the invention, there is provided an accessory of an endoscope, including a tube, the tube being provided with a portion, at the distal end thereof, having a plurality of openings.

Since there are a plurality of openings, when the tube is used for aspiration, even if one of the openings clogs, aspiration can be carried on through the other openings.

Optionally, the above accessory is further provided with a connector portion provided at a proximal end of the tube. An external device is connected with the connector portion. To the connector portion, for example, a device for aspirating fluid, a device for dispersing coloring pigment, or the like, can be connected.

Preferably, the connector includes a mouth piece coupled to the tube. According to one preferred embodiment, the mouth piece is provided coaxially with the tube. Alternatively, an axis of the mouth piece can be substantially perpendicular to the axis of the tube. It should be noted that the angular relationship between the mouth piece and the tube is not limited to the above examples, and may be determined depending on a structure and purpose of the accessory and endoscope using the accessory.

Optionally, the tube has a flexible portion at least at a distal end portion thereof, wherein a plurality of slits extending along the axis of the tube are formed on the flexible portion to define bendable band sections. A mechanism applies force in a direction where the flexible portion is compressed along the axis of the tube, and the plurality of openings are formed as the bendable band sections expand radially due to the force applied by the mechanism.

Thus, by compressing the distal end of the tube towards the proximal end side, the band sections are radially expanded, and between the band sections, a plurality of openings are formed. The mechanism may always apply the force to the tube so that the openings are neutrally formed. Alternatively, the mechanism may be constructed to open or close the band sections.

In a particular case, the mechanism includes a wire, a distal end of which is connected to the distal end of the tube. Since the accessory is used for fluid flowing therethrough, there is a clearance between the wire and the inner surface of the tube for allowing fluid to flow through. The diameter of the wire may be sufficiently smaller than the inner diameter of the tube.

Preferably, a proximal end of the wire is secured to a second tube which is connected to the tube.

In this case, the second tube may be fixed with respect to the tube. Then, the bendable band sections are radially expanded, and the status is always maintained. Alternatively, the second tube may be arranged to be movable with respect to the tube along the axial direction of the tube. In such a case, the amount of radial expansion of the bendable band sections is determined in accordance with the position of the second tube. Therefore, it may be possible to adjust the size of the openings by positioning the second tube at an appropriate position. The size of the openings may be determined in accordance with the purpose of use.

Preferably, a manipulation member may be connected to the second tube, the wire being moved along the axis of the tube as the manipulation member is operated. With the manipulation member, an operator can manipulate the size of the openings easily.

Optionally, the mechanism is further provided with a stopping structure for arresting the second tube at at least one predetermined position along the axis of the tube. Accordingly, the status of the openings can be maintained with use of the stopping mechanism. Preferably, the predetermined position is a position where the bendable band sections expand. Alternatively, the at least predetermined position includes at least a first and a second stopping positions. The amount of radial expansion of the bendable band sections when the second tube is located at the first position is greater than that when the second tube is located at the second position. Thus, different opening conditions of the openings can be maintained by arresting the second tube at respective positions.

In one particular embodiment, when the tube is used for injecting fluid, the second tube is positioned at the first position. Since the size of the openings is relatively large, fluid can be injected quickly.

When the tube is used for tinction, the second tube is located at the second position. In this case, for example, a coloring pigment can be dispersed to a relatively wide area.

Further, when the tube is used for aspiration, the second tube is located at the second position. In this case, a relatively great amount of fluid can be aspirated through the openings.

Furthermore, when the tube is used as a collecting instrument, an object can be caught when the second tube is located at the first position, and wherein an object can be grasped when the second tube is located at the second position. This structure is advantageous, since the band sections are forcibly opened, and forcibly closed. Therefore, it is ensured that the object can be collected.

Further optionally, a distal end portion of the wire is made hard to bend. Since the distal end portion of the wire tends to be bent depending on the opened condition of the band sections, if the portion is made rigid, the orientation of the wire, and therefore the bending condition of each band section is made stable.

In a particular example, the wire is provided with a sheath at the distal end portion, the distal end portion being hard to bend due to the sheath. Alternatively, the distal end portion of the wire itself is formed to be rigid or formed of a rigid material.

Still optionally, an end piece is provided at the distal end of the tube to which a distal end of the wire is connected. Further, the end piece may extend in the axial direction of the tube, starting from the distal end of the tube.

With this structure, the end piece can be a treatment instrument of the endoscope. For example, the treatment instrument may be a cautery instrument for cauterization of an affected area. Alternatively, the treatment instrument may be a lithotriptic instrument for crushing calculi.

Further optionally, the treatment instrument requires energy to operate, and wherein the wire transmits the energy for the treatment instrument.

Still optionally, a proximal end surface of the end piece is on the proximal end side of the tube with respect to a center of the bendable band sections when the bendable band sections are expanded radially.

In this case the proximal end surface is formed as a conical surface. In particular, an apical angle of the conical surface is substantially 90 degrees. In this case, if fluid is dispersed through the tube, the fluid is directed towards the direction perpendicular to the axis of the tube. Alternatively, an apical angel of the conical surface is less than 90 degrees. In this case, fluid may be concentrated a narrower area than the above case. Further alternatively, the proximal end surface of the end piece is a plane surface which is substantially perpendicular to the axis of the tube.

It is preferable that a portion of the wire adjacent to the end piece is made rigid. This realizes a stable operation of the bendable band sections.

It is preferable that a maximum width of each of the plurality of openings is not greater than an inner diameter of the tube. If a clogged object has a diameter greater than the maximum width of the openings, it never enters the tube. Further, if the clogged object has a diameter smaller than the maximum width of the openings, the object enters the tube, and is then sucked through the tube since the diameter of the object is less than the inner diameter of the tube.

Still optionally, a meshed portion is provided at the distal end of the tube, the plurality of openings being defined as meshes of the meshed member. The meshed portion may be another element connected to the tube, or a part of the tube which is formed to have meshes.

In the former case, the meshed member comprises a net that is connected to the distal end of the tube, covering an opening at the distal end of the tube. It is preferable that the net is retractable inside the tube through the opening at the distal end of the tube. If the net is retractable, when aspiration is performed, the net protrudes from the tube, and therefore an object may not enter the tube. Further, if some substance clogs on the net, by reciprocally retracting and protruding the net, the substance may be removed from the net. It should be noted that even if the net is not retaractable, clogging may be effectively prevented.

In a particular example, the distal end of the wire is connected to the net so that the net is movable between a position at which the net is retracted and another position at which the net protrudes from the distal end of the tube, in accordance with operation of the wire.

Optionally, the mechanism comprises a stopper for arresting the wire at least one predetermined position along a movable range in the axial direction of the wire.

Preferably, the predetermined position is a position at which the net protrudes from the distal end of the tube.

According to another aspect of the invention, there is provided an aspiration accessory for an endoscope, comprising a tube member and at least one opening formed on the tube member. A scraper which is movable inside the tube member, the scraper being capable of passing on the at least one opening. A manipulating member is manually operable to move the scraper with respect to the tube member.

Since the scraper is provided, substance which clogs the opening can easily be removed by operating the scraper.

Particularly, the at least one opening is formed on a circumferential surface of the tube member, and the scraper is slidablly fitted inside the tube member. In this case, sliding movement of the scraper along the axis of the tube removes the substance inside the tube from the opening. As a result, the remainder of the substance outside the tube may also be removed.

Preferably, a plurality of openings are formed on the circumferential surface of the tube member. Since the plurality of openings are formed, even if one of the opening clogs, aspiration can be carried out.

In a particular example, the scraper is located at the distal end of the tube member when the tube member is used for aspiration, and wherein upon movement of the scraper from the distal end of the tube member towards the proximal end of the tube member, an object clogged at the plurality of openings are removed therefrom by the scraper.

As described with respect to the accessory having a different structure, it is preferable that there is provided a stopper for arresting the scraper at a predetermined position along the axis of the tube member. With this structure, the scraper may be fixed when the aspiration accessory is in use (i.e., aspiration is carried out).

BRIEF DESCRIPTION OF THE DRAWINGS

FIG. 2 is a sectional side view of a distal end portion of the treatment accessory of FIG. 1 in a closed state;

FIG. 3 is a section view taken along line III—III in FIG. 2;

FIG. 9 is a sectional side view of a treatment accessory according to a third embodiment of the invention;

FIG. 9A shows a groove formed on the treatment accessory shown in FIG. 9;

FIG. 14A shows a groove formed on the treatment accessory shown in FIG. 14;

FIG. 15 is a sectional side view the treatment accessory of FIG. 14 in different state;

FIG. 15A shows a groove formed on the treatment accessory shown in FIG. 15;

FIG. 34 is a side view of the distal end portion of the treatment accessory of FIG. 19 illustrating collection of a particle;

FIG. 35 is a sectional view taken along line XXX-V–XXXV of FIG. 34;

FIG. 36 is a side view of the distal end portion of the treatment accessory of FIG. 19 illustrating collection of a plurality of particles;

FIG. 37 is a sectional side view of a treatment accessory according to a seventh embodiment of the invention;

FIG. 37A shows a groove formed on the treatment accessory shown in FIG. 37;

DETAILED DESCRIPTION OF THE PREFERRED EMBODIMENTS

Figure 1:
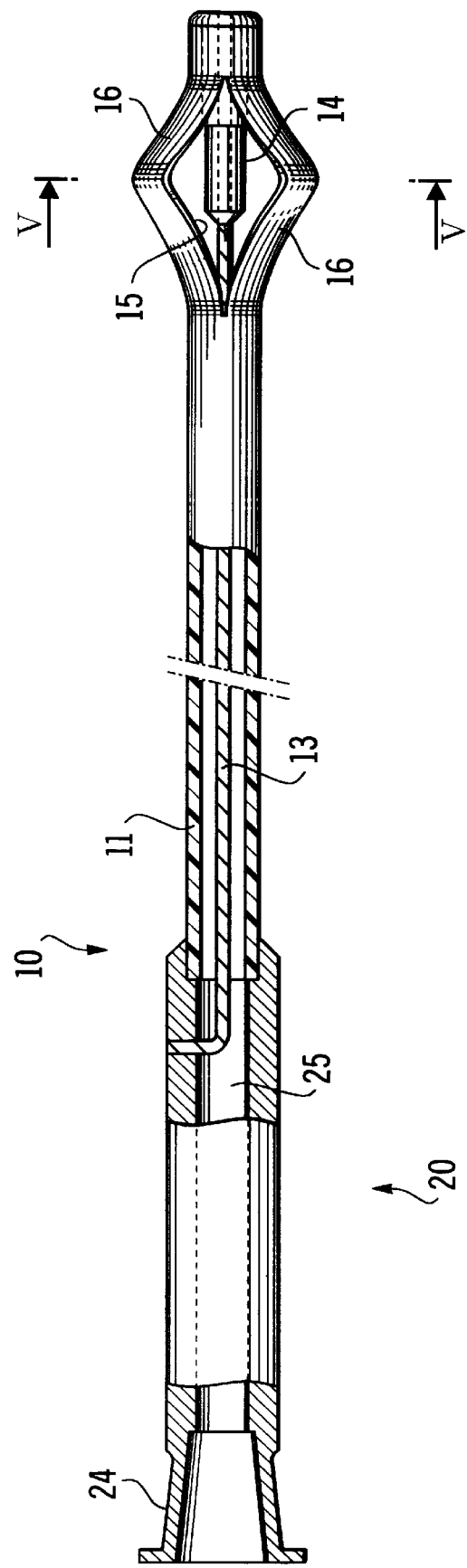
FIG. 1 is a sectional side view of a treatment accessory according to a first embodiment of the invention.
Figure 6:
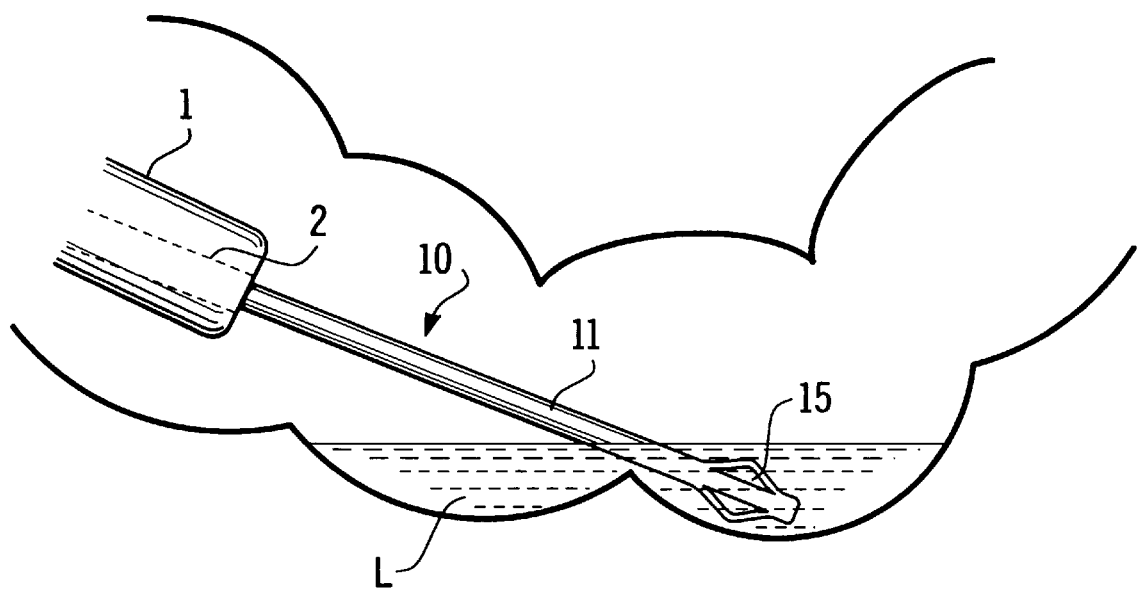
FIG. 6 is a schematic drawing showing use of the treatment accessory of FIG. 1.

FIG. 1 shows a treatment accessory 10 according to a first embodiment of the invention. The treatment accessory 10 includes a flexible tube 11 and a cylindrical manipulation portion 20 coaxially attached at a proximal end of the flexible tube 11. The flexible tube 11 is made of, for example, nylon, HDPE (polyethylene), polyurethane resin or tetrafluoroethylene resin, and is designed to be flexible, at least at a distal end portion thereof. When using the treatment accessory 10, the flexible tube 11 is inserted through an insertion channel 2 of an endoscope 1 (as shown in FIG. 6).

As shown in FIG. 1, a proximal end of a wire 13 is also attached to the manipulating portion 20 and the wire 13 extends through the entire length of the flexible tube 11 and a distal end of the wire 13 is attached to a tip 14 provided at a distal end of the flexible tube 11.

In particular, the diameter of the wire 13 is sufficiently small with respect to the inner diameter of the flexible tube 11 to allow a liquid or the like to flow along the length of the flexible tube 11.

[0010]

Figure 4:
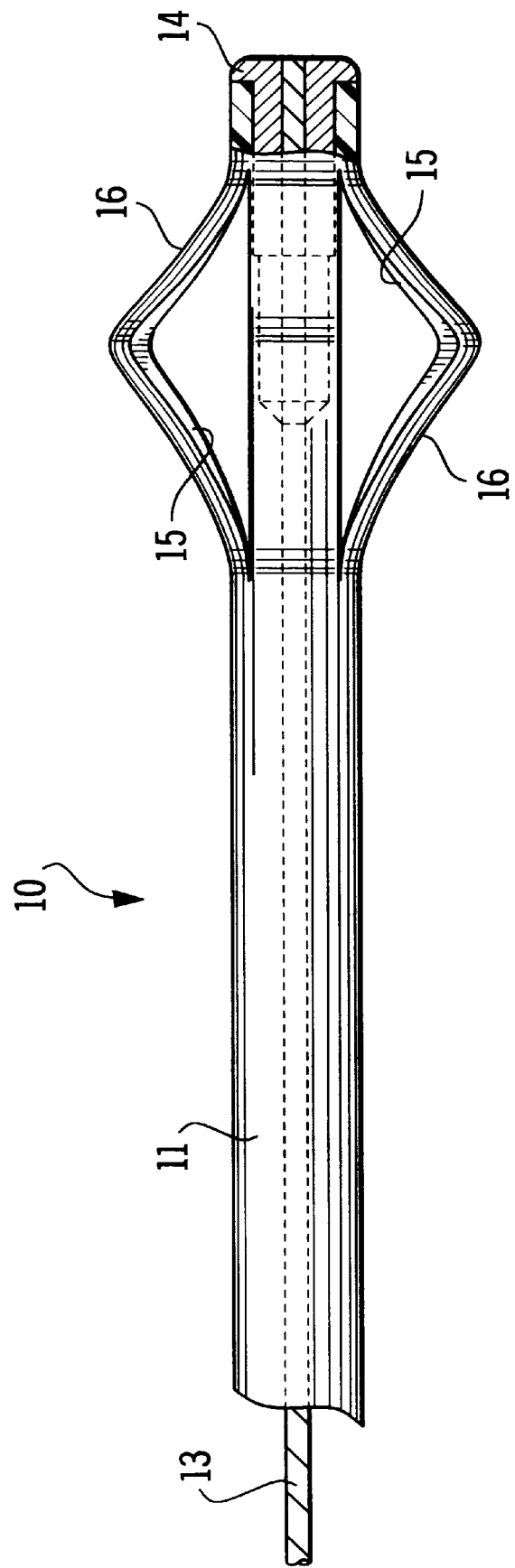
FIG. 4 is a side view of the distal end portion of the treatment accessory of FIG. 1 as rotated by 45 degrees.
Figure 5:
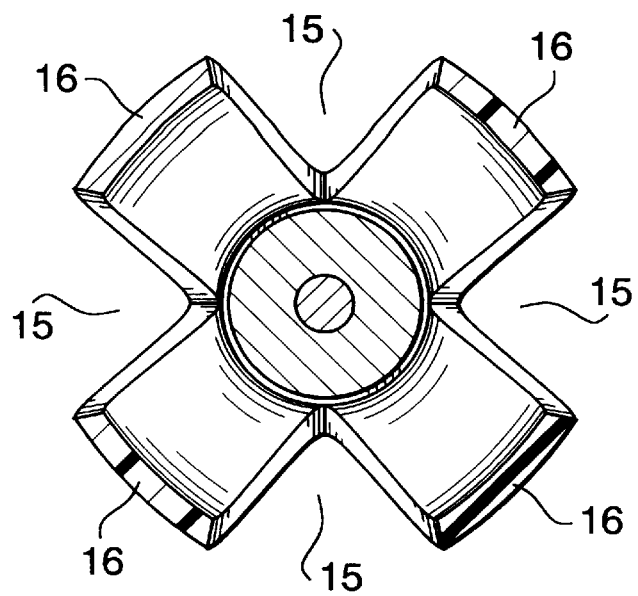
FIG. 5 is a section view taken along line V—V in FIG. 1.

FIG. 2 is an enlarged sectional side view of a distal end portion of the flexible tube 11 in a closed state. FIG. 3 is an enlarged sectional view along line III—III of FIG. 2. FIG. 4 is an enlarged side view of the distal end portion of the flexible tube 11 in an expanded state (the same state as shown in FIG. 1). FIG. 5 is an enlarged front view along line V—V of FIG. 1.

As shown in FIGS. 1, 2, 3, 4, and 5 the distal end portion of the flexible tube 11 is formed having a plurality of slits 15 extending parallel to the axis of the flexible tube 11 for a predetermined length. In this embodiment, as an example, four slits 15 are formed separated by 90 degrees about the circumference of the flexible tube 11. However, a different number or arrangement of the slits 15 may be provided. The slits 15 define four band sections 16 between adjacent slits 15.

The wire 13 and the flexible tube 11 are fixed to the manipulation portion 20 such that, in a neutral state, i.e., when no external force is applied, the distal end portion of the flexible tube 11 has a shape such as that shown in FIGS. 1, 4, and 5. That is, the band sections 16 are bent and the slits 15 expand to form openings. When an external force is applied, for example by squeezing the band sections 16 with fingers or the like, the distal end portion of the flexible tube 11 has a shape such as that shown in FIGS. 2 and 3. That is, the band sections 16 extend distally and the slits 15 are closed.

Further, as shown in FIG. 1, a connection mouthpiece 24 which may be connected to an external apparatus (not shown) is formed at a proximal end of the manipulation portion 20 and a passage 25 is provided through the manipulation portion 20 to connect the connection mouthpiece 24 with the flexible tube 11.

When the treatment accessory 10 passes through the insertion channel 2 of an endoscope 1, the band sections 16 are pressed together by an operator to have a shape similar to that shown in FIG. 2, allowing the flexible tube 11 to be easily fed through the insertion channel 2.

Once the distal end portion of the flexible tube 11 has passed out of a distal end of the insertion channel 2, the band sections 16 return to the neutral expanded shape, as shown in FIG. 6.

As shown in FIG. 6, the treatment accessory 10 may be used for suction of cleaning solutions, pigment solutions, or other liquids from body cavities. In this case, an aspiration (suction) apparatus (not shown) is connected to the connection mouthpiece 24, and as shown in FIG. 6, a liquid L is sucked into the flexible tube 11 through the open slits 15.

In this case, since there are four slits 15, there are four inlets for aspirating the liquid L into the flexible tube 11. Thus, even if one of the slits 15 is clogged with particles, such as food residue or the like, the other three slits 15 function to allow aspiration to continue without removing the treatment accessory 10 from the endoscope 1.

Figure 7:
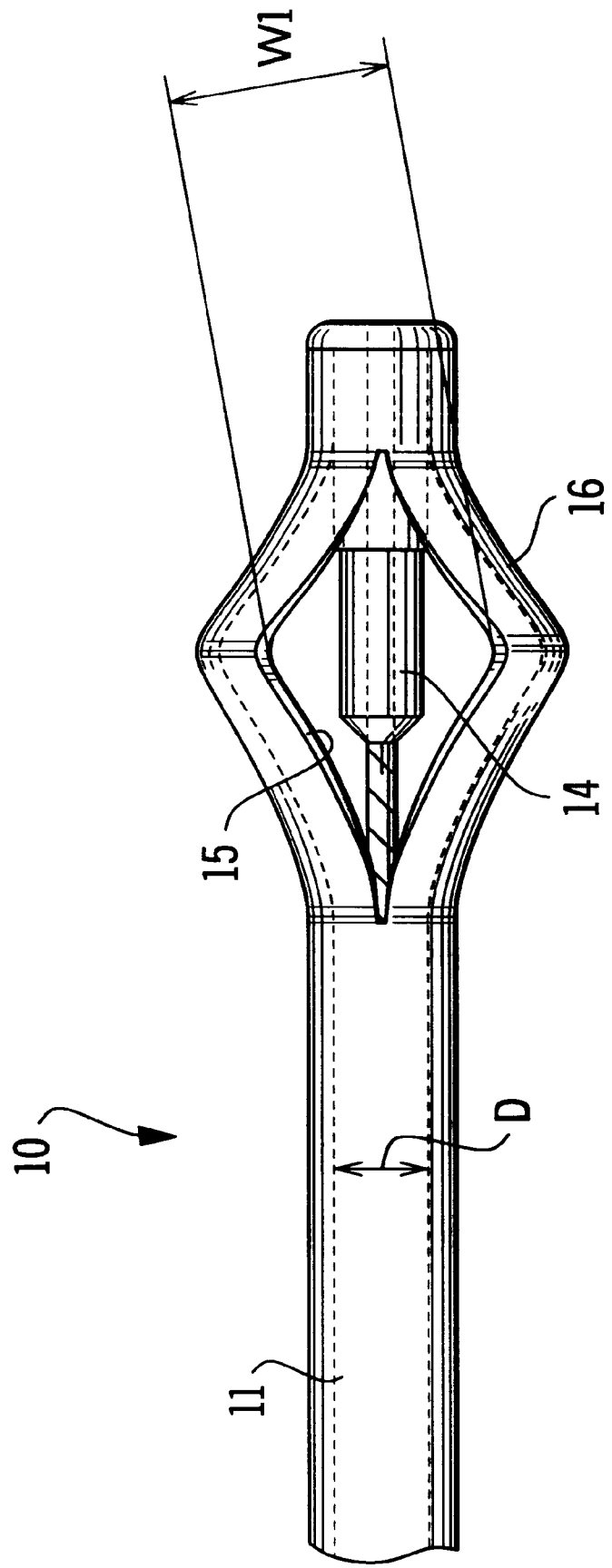
FIG. 7 is a side view of a distal end portion of a treatment accessory of FIG. 1 illustrating dimensions.

FIG. 7 shows the distal end portion of the treatment accessory 10. In particular, it is beneficial if the flexible tube 11 is formed such that D>W1, where D is an inner diameter of the flexible tube 11 and W1 is a maximum clearance between adjacent band sections 16. Thus, even if particles pass through the slits 15, the particles will also pass through the flexible tube 11 without clogging.

Figure 8:
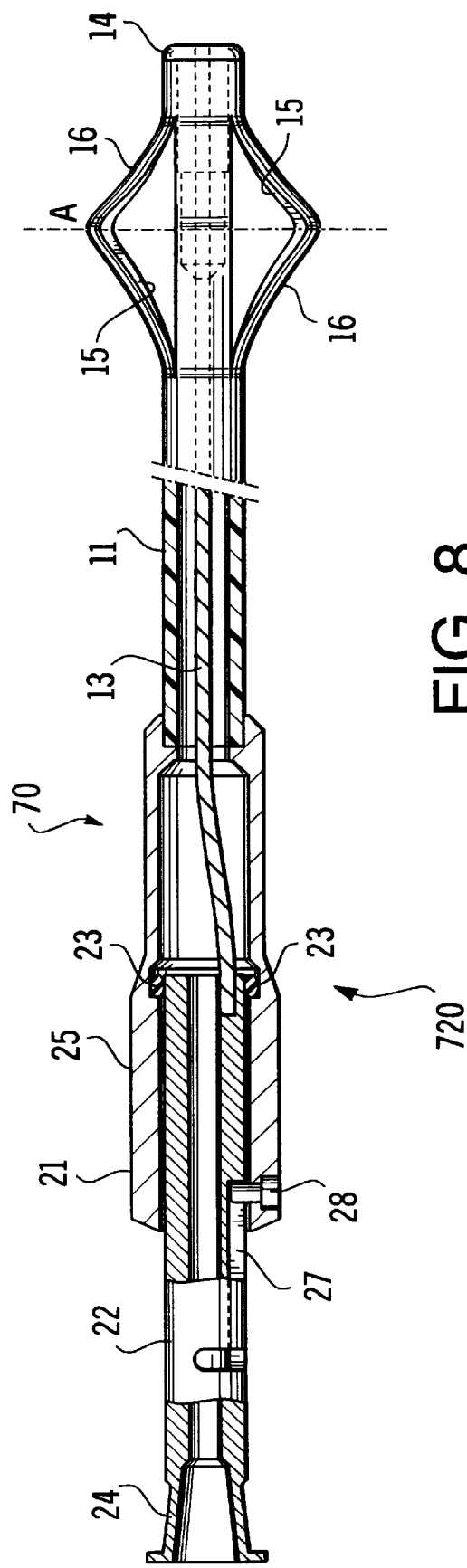
FIG. 8 is a sectional side view of a treatment accessory according to a second embodiment of the invention.

FIG. 8 shows a treatment accessory 70 according to a third embodiment of the invention. In this embodiment, the manipulation portion 720 is formed differently than the manipulation portion 20 of the first embodiment.

In this embodiment, the manipulation portion 720 includes an outer cylinder 21 to which the base end of the flexible tube 11 is connected and an inner cylinder 22 to which the base end of the wire 13 is connected and which is slidably arranged coaxially with the outer cylinder 21.

Thus, the wire 13 is axially movable with respect to the flexible tube 11 by moving the inner cylinder 22 with respect to the outer cylinder 21. An O-ring 23 is mounted between the outer cylinder 21 and the inner cylinder 22 to provide a liquid seal.

In this embodiment, the connection mouthpiece 24 is formed at a proximal side of the inner cylinder 22 and the passage 25 is provided through the inner cylinder 22 providing a fluid path to the flexible tube 11.

Figure 8A:
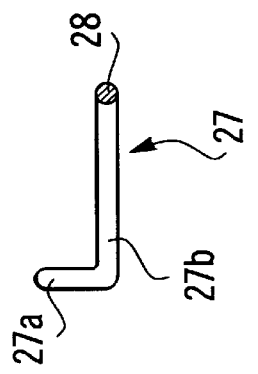
FIG. 8A shows a groove formed on the treatment accessory shown in FIG. 8.

As shown in FIGS. 8 and 8A, an L-shaped groove 27 is formed on an outer surface of the inner cylinder 22 and a pin 28 protrudes inward from the outer cylinder 21 to engage with the groove 27.

The groove 27 and the pin 28 are arranged such that, when the pin 28 is engaged with a lateral part 27a of the groove 27, the inner cylinder 22 is not axially movable. In this embodiment, at this point, the wire 13 is extended to the distal side such that band sections 16 extend closing the slits 15.

Further, as shown in FIGS. 8 and 8A, when the pin 28 is engaged with a linear part 27b of the groove 27, the inner cylinder 22 is axially movable and the band sections 16 expand outwardly to open the slits 15.

In this embodiment, since the band sections 16 may be expanded or contracted by operation of the manipulation portion 720, if particles clog the slits 15, the clogging can be eliminated by forcibly expanding and contracting the band sections 16.

Further, the maximum width W1 may be formed greater than the inner diameter D (i.e., D<W1) since if particles clog the slits 15 or the flexible tube 11, reciprocating the wire 13 causes the particles to be crushed or divided, thereby eliminating the clogging.

In this embodiment, as shown in FIG. 8, a proximal end of the tip 14 extends past a central point A of the expanded slits 15 such that when the wire 13 is drawn toward the proximal side the four band sections 16 expand evenly.

FIG. 9 shows a treatment accessory 80 according to a third embodiment of the invention. In this embodiment, the manipulation portion 720 is similar to that of the previous embodiment and is not described in detail.

In this embodiment, a distal end portion of a flexible tube 811 is provided with at least one aspiration opening, in this case, four aspiration openings 12. The aspiration openings 12 have a diameter that is slightly smaller than an inner diameter of the flexible tube 811 and are formed along the sides of the flexible tube 811.

Further, rather than being attached to a tip 14, the wire 13 is attached to a scraper 15 that is slidably fitted in the flexible tube 811.

Thus, in this embodiment, when the pin 28 is positioned at the lateral part 27a of the groove 27 (shown in FIG. 9A), the scraper 15 is positioned, as shown in FIG. 9, at a distal side of the aspiration openings 12.

Figure 10:
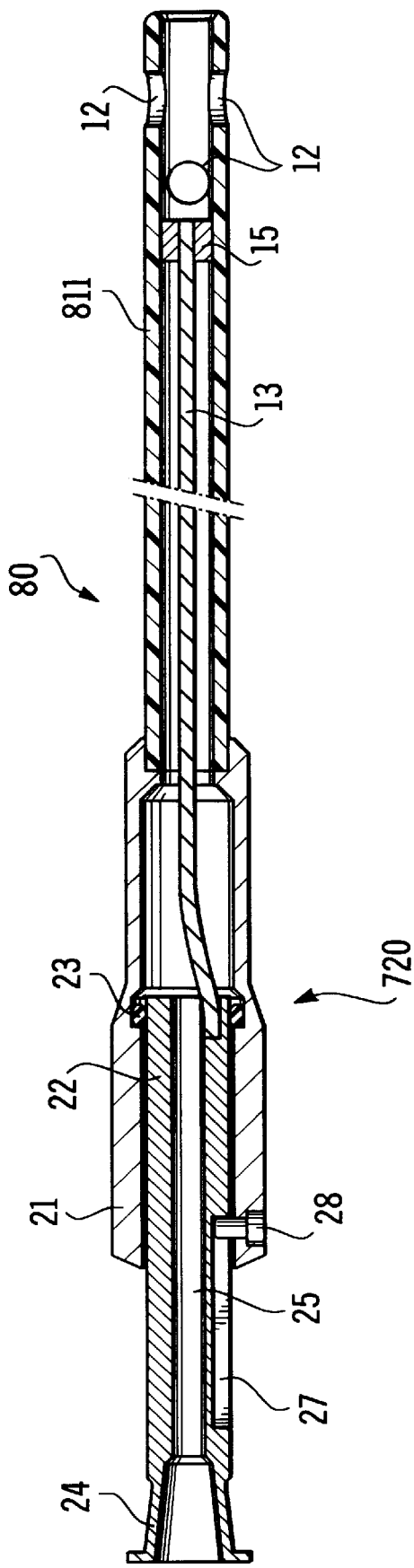
FIG. 10 is a sectional side view the treatment accessory of FIG. 9 in different state.
Figure 10A:
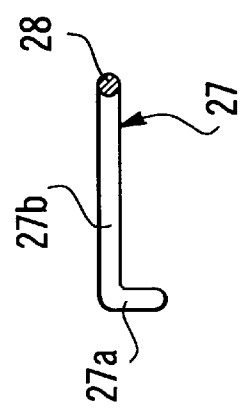
FIG. 10A shows a groove formed on the treatment accessory shown in FIG. 10.

Further, as shown in FIG. 10, by operation of the manipulation portion 720, the scraper 15 may be drawn in the proximal direction to pass over the inside of the aspiration openings 12 and move to a position on the proximal side thereof. Note that also in this embodiment, the groove 27 (shown in FIG. 10A) is formed, which functions in a simillar manner in the embodiment shown, for example, in FIG. 9A.

Figure 11:
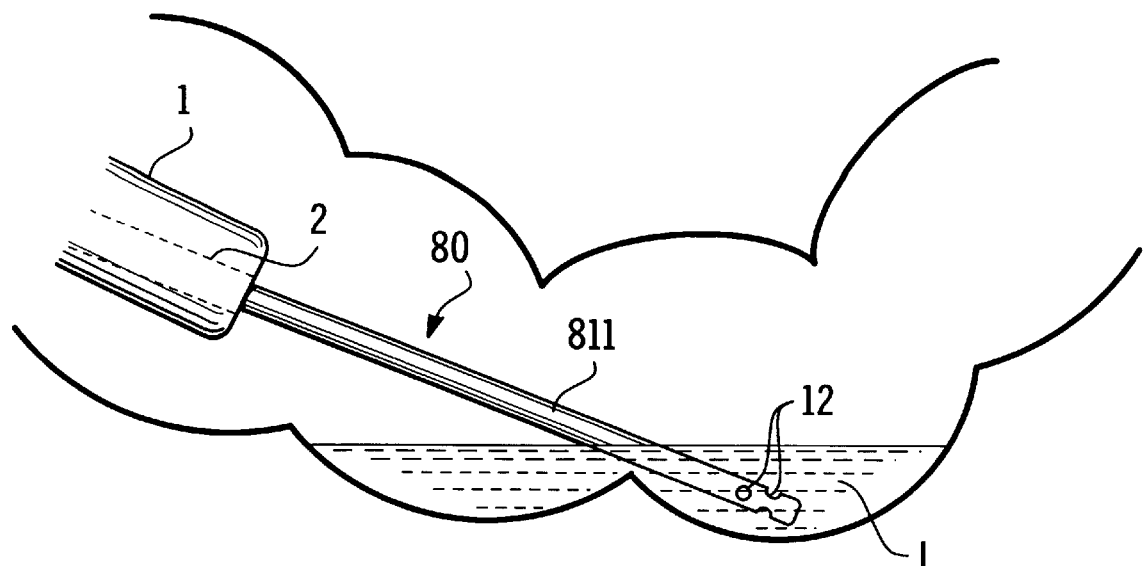
FIG. 11 is a schematic drawing showing use of the treatment accessory of FIG. 9.

In use, the treatment accessory 80 is inserted through and protruded from the channel 2 of the endoscope 1 with the scraper 15 positioned at the distal end of the flexible tube 811 (FIG. 9) and the aspiration openings 12 are inserted into the liquid L or the like in a body cavity, as shown in FIG. 11.

Figure 12:
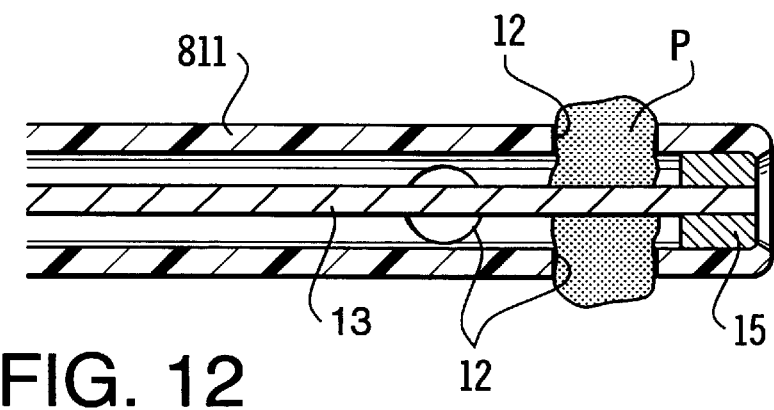
FIG. 12 is a side view of a distal end of the treatment accessory of FIG. 9 in use.
Figure 13:
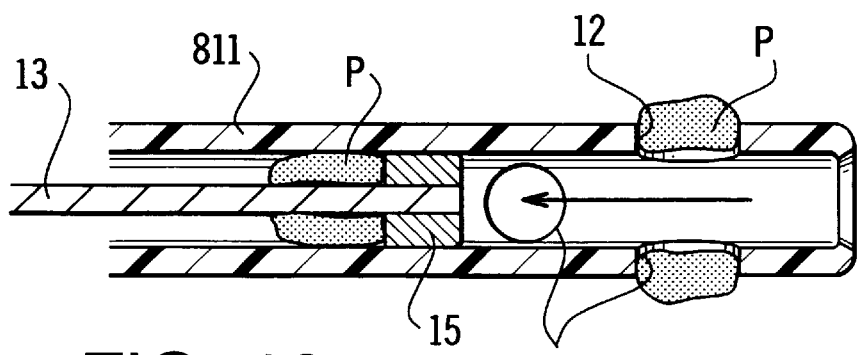
FIG. 13 is a side view of a distal end of the treatment accessory of FIG. 9 when dislodging clogging particles.

If a particle P clogs one or more of the aspiration openings 12 of the flexible tube 11, as shown in FIG. 12, the inner cylinder 22 is moved to move the scraper 15 to a proximal position, as shown in FIG. 10. Thus, as shown in FIG. 13, the particle P is scraped by the scraper 15, and broken such that a portion is pushed up the flexible tube 11, aspirated, and removed. If the particle P is not immediately aspirated and removed, the scraper 15 may be reciprocated axially several times.

The scraper 15 is then returned to a distal position (FIG. 9) of the flexible tube 11, and any portions of the particle P remaining at the aspiration openings 12 will be smaller and can be aspirated and removed, or the process may be repeated.

Figure 14:
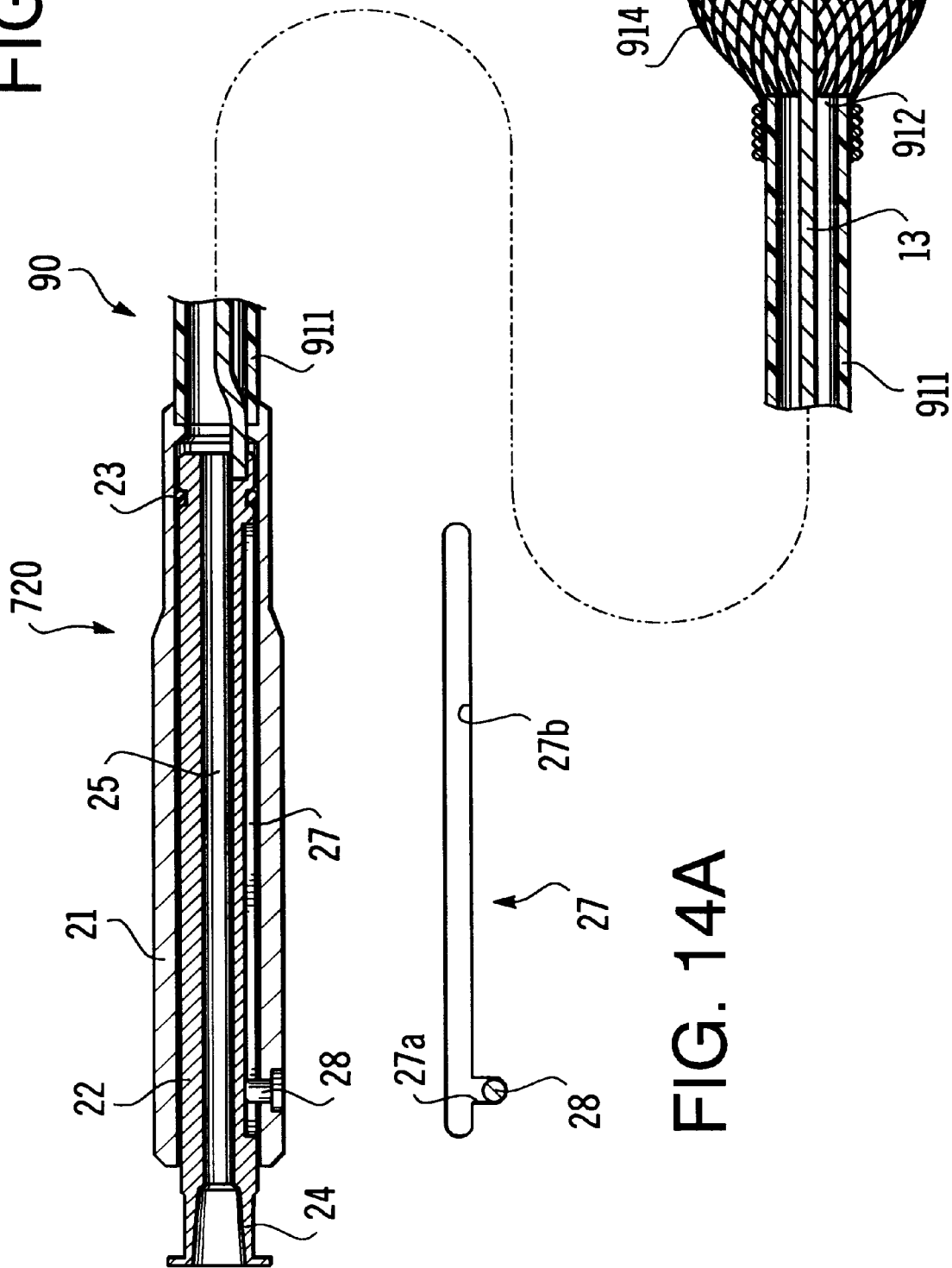
FIG. 14 is a sectional side view of a treatment accessory according to a fourth embodiment of the invention.

FIG. 14 shows a treatment accessory 90 according to a fourth embodiment of the invention. In this embodiment, the manipulation portion 720 is similar to that of the second and third embodiments, however, the inner cylinder 22, outer cylinder 21, and the groove 27, which is shown in FIG. 14A, may need to be longer in order to provide for the required movement of the wire 13.

In this embodiment, a distal end portion of a flexible tube 911 is provided with at least one aspiration opening 912. In this case, the aspiration opening 912 is at the distal end of the flexible tube 911.

The flexible tube 911 is also provided with an expandable and contractible mesh filter 914 mounted at the distal end portion of the flexible tube 911 such that the aspiration opening 912 is covered thereby. The mesh filter 914 is, for example, a mesh tube formed by braiding thin wires, for example, stainless steel, into a mesh. One end of the mesh tube is tightly bound to the distal end of the wire 13 and the other end is then folded back and tightly bound to a circumferential surface of the flexible tube 911 such that the aspiration opening 912 is covered by the mesh filter 914.

The wire 13, the flexible tube 911, and the mesh filter 914 are arranged such that the mesh filter 914 may be expanded by extending the wire 13 from the distal end of the flexible tube 911, as shown in FIG. 14, and retracted into the flexible tube 911 (in this case, through the aspiration opening 912) by drawing the wire 13 into the flexible tube 911, as shown in FIG. 15.

Figure 16:
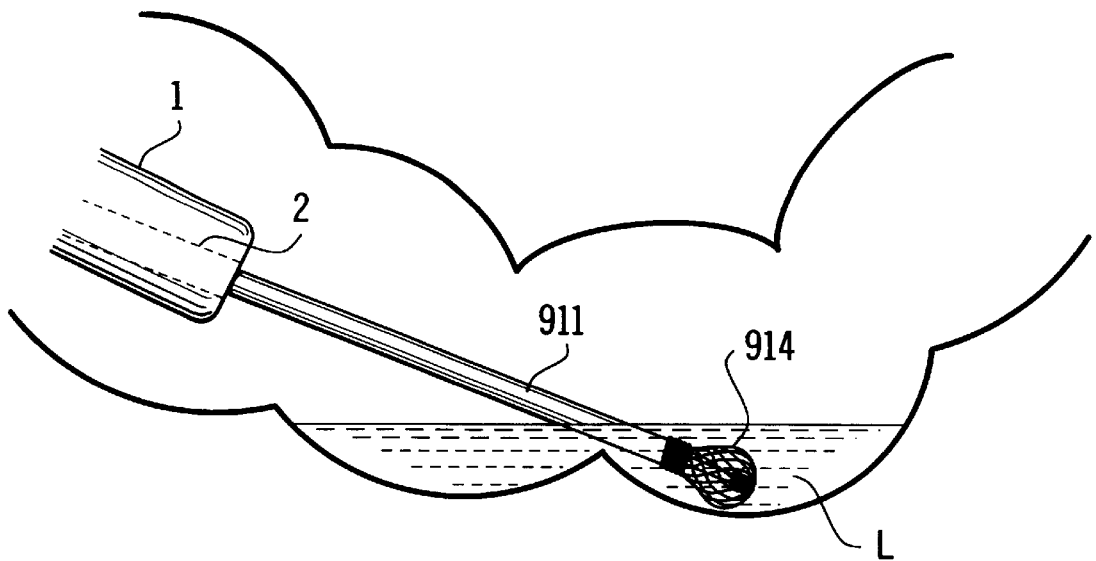
FIG. 16 is a schematic drawing showing use of the treatment accessory of FIG. 14.

In use, the treatment accessory 90 is inserted through the channel 2 of the endoscope 1 with the mesh filter 914 drawn into the flexible tube 911 and then, when protruded from the channel 2 and inserted into the liquid L or the like in a body cavity, the mesh filter 14 is extended from the distal end of the flexible tube 911 (as shown in FIG. 16).

With this arrangement, even if particles, such as food residue and the like, in the liquid L are drawn toward the aspiration opening 912, since the mesh filter 914 has a relatively large area, the aspiration opening 912 is not clogged.

Figure 17:
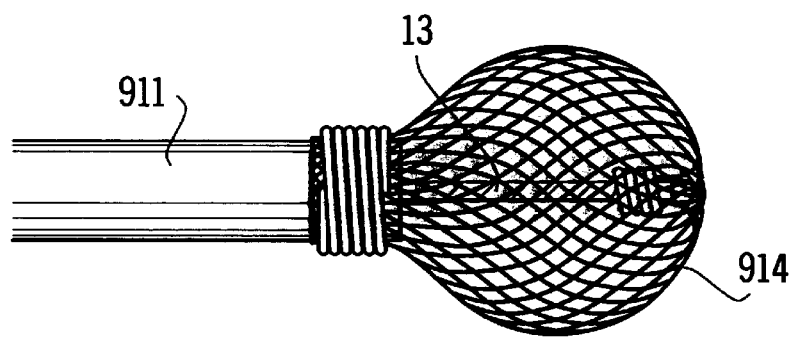
FIG. 17 is a side view of a distal end of the treatment accessory of FIG. 14 in use.
Figure 18:
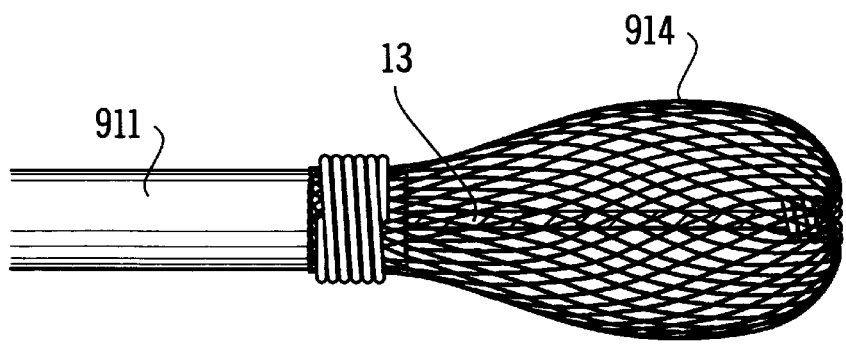
FIG. 18 is a side view of a distal end of the treatment accessory of FIG. 14 when dislodging clogging particles.

Further, if particles clog the mesh filter 914 during the aspiration of the liquid L, the clogging can be eliminated by reciprocating movements of the wire 13 (i.e., the inner cylinder 22) along the axis to deform the mesh filter 914, as shown in FIGS. 17 and 18, to dislodge any particles or the like.

It should be noted that also in this embodiment the groove 27 (shown in FIG. 15A) is provided as in some of the other embodiments.

Figure 19:
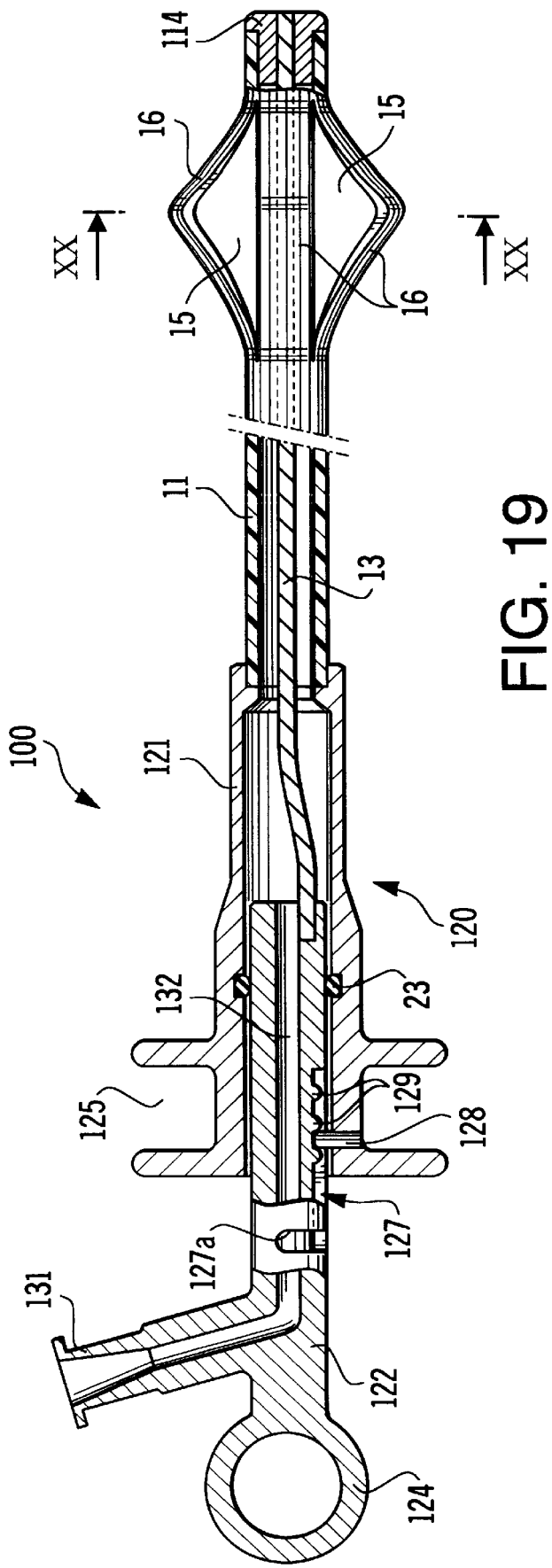
FIG. 19 is a sectional side view of a treatment accessory according to a fifth embodiment of the invention.

FIG. 19 is a sectional view of a treatment accessory 100 according to a fifth embodiment of the invention.

Figure 26:
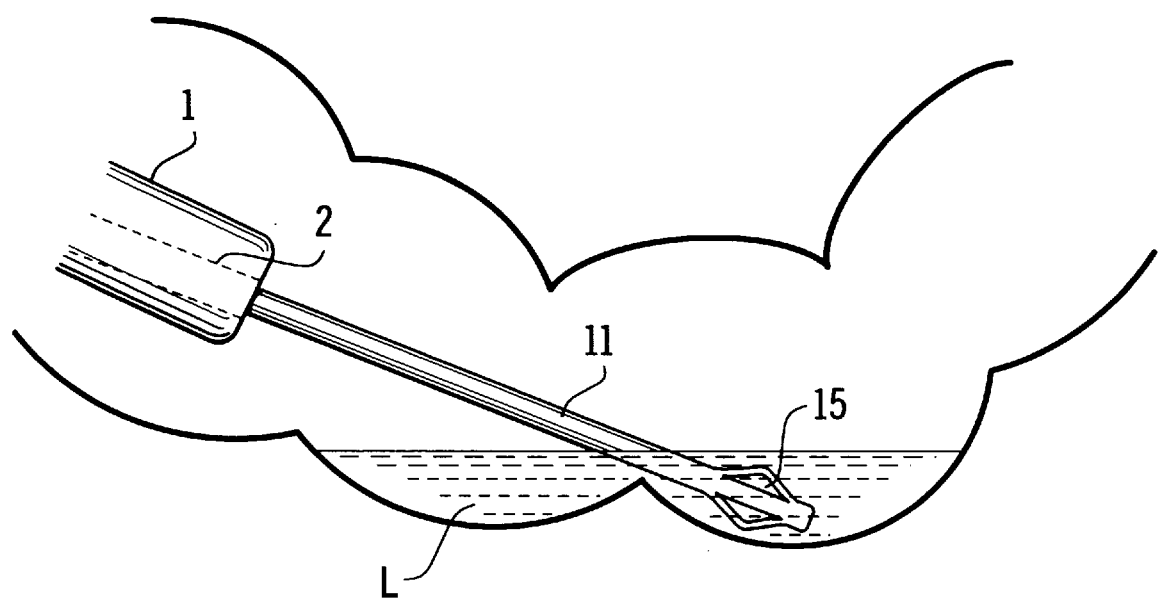
FIG. 26 is a schematic drawing showing use of the treatment accessory of FIG. 19 for aspiration.

The treatment accessory 100 includes the flexible tube 11 of the first embodiment and a manipulation portion 120 attached at a proximal end of the flexible tube 11. As described above, the flexible tube 11 is made of, for example, nylon, HDPE (polyethylene), polyurethane resin or tetrafluoroethylene resin, and is designed to be flexible, at least at a distal end portion thereof. When using the treatment accessory 100, the flexible tube 11 is inserted through the insertion channel 2 of the endoscope 1 (as shown in FIG. 26).

The manipulating section 120 includes an outer cylinder 121 and a piston-shaped manipulating shaft 122 which is slidably inserted in the outer cylinder 121. A sealing O-ring 23 is provided between the outer cylinder 121 and the manipulating shaft 122.

A ring-shaped first grip 124 is provided at the proximal end of the manipulating shaft 122 for engagement with, for example, a thumb of an operator. Further, a second grip 125 is provided around the perimeter of the outer cylinder 121. In this embodiment, the second grip 125 includes two flanges protruding from the outer cylinder 121 for engagement with, for example, a forefinger and a middle finger of the operator.

An L-shaped groove 127 is formed on the outer circumference of the manipulating shaft 122 (shown in detail in FIGS. 19 and 19A), and the outer cylinder 121 is provided with a pin 128 protruding inward to engage with the groove 127.

The groove 127 is provided with a plurality of small protrusions 129 (stoppers). In this embodiment, three protrusions 129 are provided along a base of a linear part 127*b* of the groove 127. The protrusions 129 are formed such that, during movement of the manipulating part 122 relative to the outer cylinder 121, the pin 128 catches between adjacent protrusions 129 to arrest movement of the manipulating shaft 122. However, the manipulating shaft 122 may be moved by applying a slight force such that the pin 128 passes over a protrusion 129. Consequently, the pin 128 and the protrusions 129 function as a clicking mechanism for controlling movement of the manipulating shaft 122.

As shown in FIG. 19, the flexible tube 11 is coaxially attached to the outer cylinder 121. In this embodiment, the proximal end of the wire 13 is attached to the manipulating part 122 and the wire 13 extends through the entire length of the flexible tube 11 and a distal end of the wire 13 is attached to a tip 114 provided at the distal end of the flexible tube 11. As described in more detail below, the tip 114 of this embodiment is different from the tip 14 of the first and second embodiments. In particular, in this embodiment, the proximal side of the tip 114 is formed as a vertical plane with respect to the axis of the wire 13 and is situated proximal to the distal ends of the slits 15.

As above, the diameter of the wire 13 is sufficiently small with respect to the inner diameter of the flexible tube 11 to allow a liquid or the like to flow along the length of the flexible tube 11.

With the arrangement of this embodiment, axial movement of the manipulating part 122 with respect to the outer cylinder 121 causes axial movement of the wire 13 with respect to the flexible tube 11 and causes a force to be applied to the distal end of the flexible tube 11, thus, expanding the band sections 16.

Figure 20:
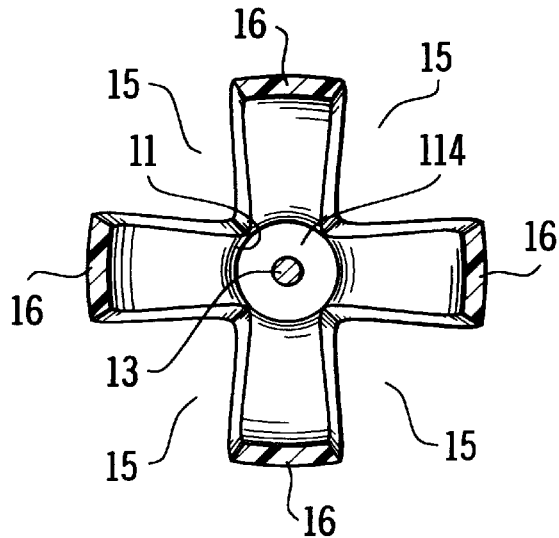
FIG. 20 is a section view taken along line XX—XX in FIG. 19.
Figure 21:
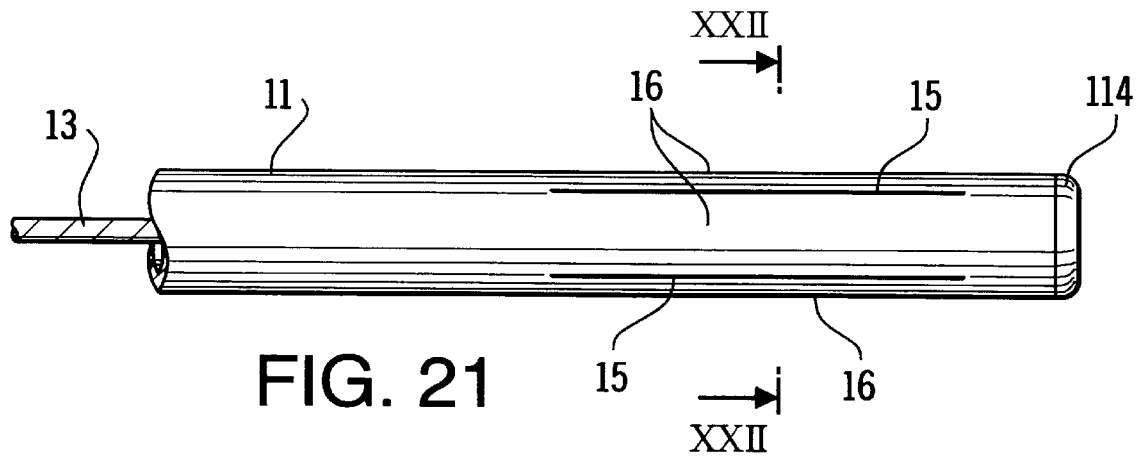
FIG. 21 is a side view of a distal end portion of the treatment accessory of FIG. 19 in a closed state.
Figure 22:
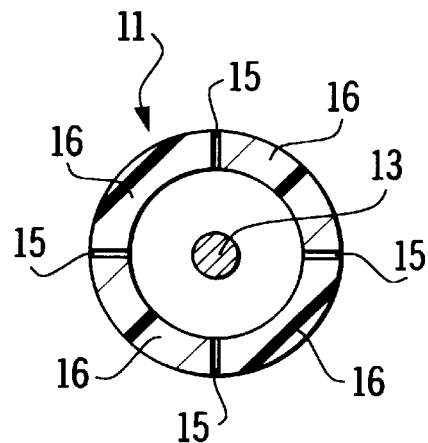
FIG. 22 is a section view taken along line XXII—XXII in FIG. 21, rotated by 45 degrees for clarity.

FIG. 20 is a front view of the distal end portion of the flexible tube 11 in an expanded state (the same state as shown in FIG. 19). FIG. 21 is a side view of the distal end portion of the flexible tube 11 in a closed state. FIG. 22 is an enlarged front view along line XXII—XXII of FIG. 21, however, the view of FIG. 22 has been rotated by 45 degrees to avoid confusion between the slits 15 and the section lines.

As shown in FIGS. 19, 20, 21, and 22, and as in the first and second embodiments, the distal end portion of the flexible tube 11 is formed having the plurality of slits 15 extending parallel to the axis of the flexible tube 11 for a predetermined length. As above, as an example, the four slits 15 are formed to be separated by 90 degrees about the circumference of the flexible tube 11, however, a different number or arrangement of the slits 15 may be provided. Further, the slits 15 define the four band sections 16 between adjacent slits 15.

Thus, when the wire 13 is pushed toward the distal end of the flexible tube 11, the distal end portion of the flexible tube 11 has a shape such as that shown in FIGS. 21 and 22. That is, the band sections 16 extend distally and the slits 15 are closed. When the wire 13 is pulled toward the proximal end of the flexible tube 11, the distal end portion of the flexible tube 11 has a shape such as that shown in FIGS. 19 and 20. That is, the band sections 16 are bent and the slits 15 expand to form openings.

In particular, when the pin 128 is interlocked with the lateral part 127*a* of the groove 127, the manipulating shaft 122 cannot be moved in the axial direction, and the band sections 16 extend distally such that the slits 15 are closed.

Figure 19A:
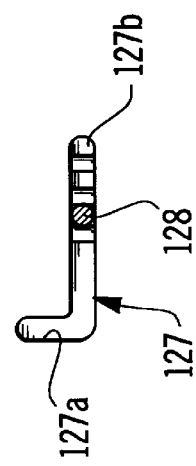
FIG. 19A shows a groove formed on the treatment accessory shown in FIG. 19.

As shown in FIGS. 19 and 19A, when the pin 128 is engaged with the linear part 127*b* of the groove 127, the manipulating shaft 122 is movable in the axial direction, and as moved the band sections 16 expand outward due to the force applied by the wire 13.

As described above, the protrusions 129 function as a clicking mechanism for controlling movement of the manipulating shaft 122 such that by applying a slight force to the manipulating shaft 122, it is possible to freely select from among, in this case, three levels for the degree of expansion of the band sections 16.

As shown in FIG. 19, the manipulation portion 120 is further provided with a connecting nozzle 131 that protrudes from the manipulating shaft 122. A channel 132 is formed extending along the axes of the manipulating shaft 122 and the connecting nozzle 131 such that by connecting the connecting nozzle 131 with an external apparatus (not shown) liquids or the like may be fed into or sucked out of the flexible tube 11.

When the treatment accessory 100 passes through the insertion channel 2 of the endoscope 1, the manipulating portion 120 is set such that the pin 128 is engaged with the lateral part 127*a* of the groove 127 so that the band sections 16 extend distally, as in FIG. 21, allowing the flexible tube 11 to be easily fed through the insertion channel 2.

Once the distal end portion of the flexible tube 11 has passed out of a distal end of the insertion channel 2, the manipulation shaft 122 is rotated so that the pin 128 engages with the linear part 127*b* of the groove 127 and the manipulation shaft 122 is then moved along the axis in relation to the outer cylinder 121 such that the band sections 16 expand, as shown in FIG. 26. As explained above, the band sections 16 can be set at three different degrees of expansion by engaging the pin 128 with respective protrusions 129.

Figure 23:
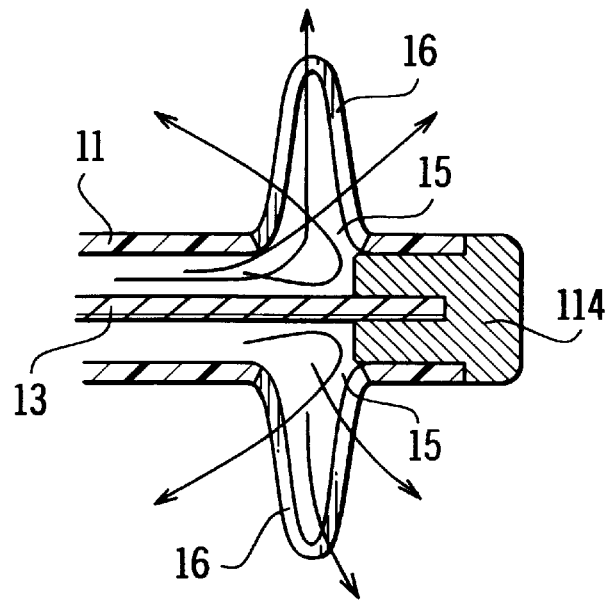
FIG. 23 is a sectional side view of the distal end portion of the treatment accessory of FIG. 19 illustrating a dispensing operation.

For example, when the treatment accessory 100 is used for cleaning or dispersing, a feeding apparatus containing cleaning solution, pigment solution, or the like (not shown) is connected to the connecting nozzle 131 and the cleaning solution is fed from the connecting nozzle 131, through the channel 132, the outer cylinder 121, and the flexible tube 11, and, as shown in FIG. 23, is ejected through the slits 15.

As shown by the arrows in FIG. 23, a portion of the solution is ejected directly outward from the slits 15, while another portion is ejected outward after hitting the proximal side of the tip 114. Further, by adjusting the degree of expansion of the band sections 16, i.e., the openness of the slits 15, the direction and width of ejection can be adjusted.

In a particular case, when the treatment accessory 100 is used to clean a specific site, for example, on a membrane surface in a body cavity, the pin 128 is interlocked with the most distal protrusion 129 so that the amount of force applied by the wire 13 is a maximum, and the band sections 16 are anchored at a maximum expanded state.

Figure 24:
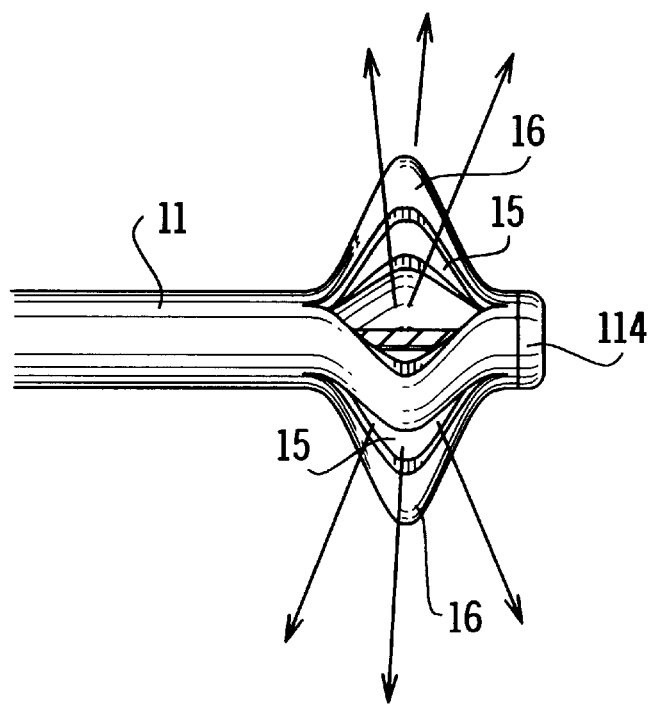
FIG. 24 is a side view of the distal end portion of the treatment accessory of FIG. 19 illustrating a lateral dispensing operation.

In this case, as shown by the arrows in FIG. 24, since the length of the openings of the slits 15 along the axis direction is shorter, the cleaning solution is forced almost laterally to allow directed cleaning of a specific site (not shown) at the side of the flexible tube 11.

In another particular case, when the treatment accessory 100 is used to disperse pigment to stain a wide area of a membrane surface of a body cavity, the pin 128 is interlocked with the most proximal protrusion 129 so that the amount of force applied by the wire 13 is reduced, and the band sections 16 are only slightly bent. In this case, as shown in FIG. 25, since the length of the openings of the slits 15 along the axis direction is longer, the pigment solution (or tinction) is dispersed over a wide range to allow shade-less staining of the membrane surface.

Figure 25:
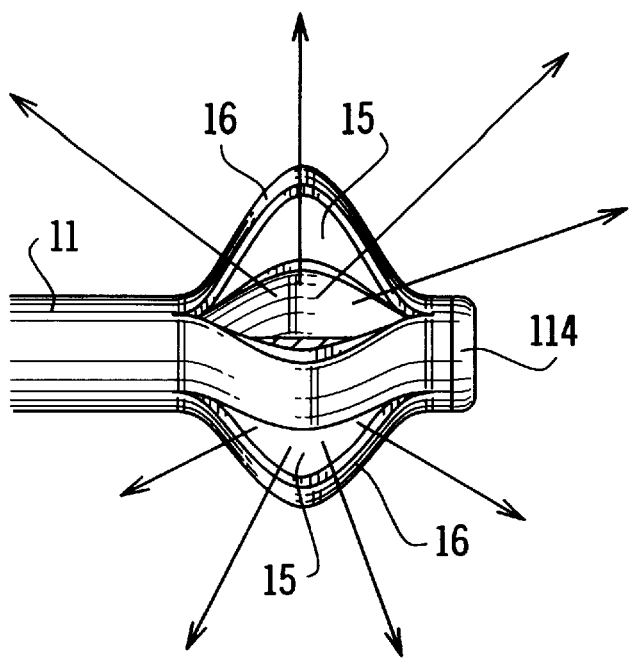
FIG. 25 is a side view of the distal end portion of the treatment accessory of FIG. 19 illustrating a dispersed dispensing operation.

When aspiration is performed, the band sections 16 may be radially expanded as shown in FIG. 25.

In a further example, when the treatment accessory 100 is used for aspiration (suction) of cleaning solutions, pigment solutions, or other liquids from body cavities, an aspiration apparatus (not shown) is connected to the connecting nozzle 131, and as shown in FIG. 26, the liquid L is sucked into the flexible tube 11 through the open slits 15. In this case, the degree of openness of the slits 15 may be adjusted in order to prevent particles (not shown) or the like from entering and clogging the flexible tube 11. In this case, the operation of the treatment accessory 100 is similar to that of the treatment accessories 10, 70 of the first and second embodiments.

Figure 27:
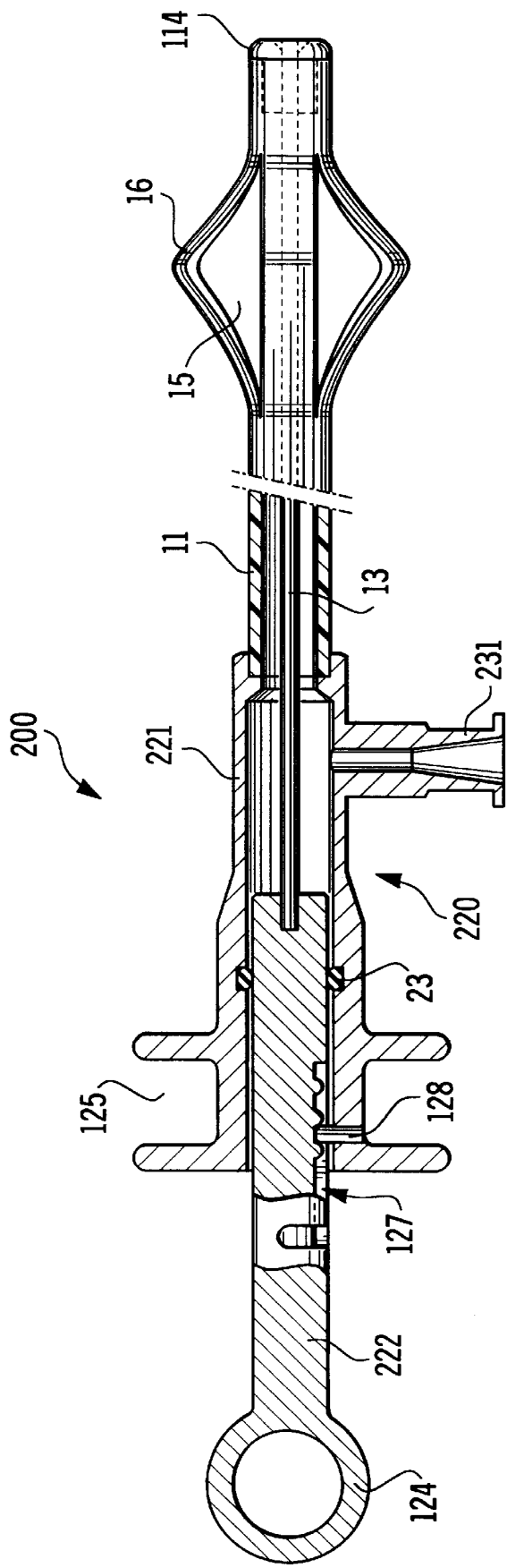
FIG. 27 is a sectional side view of a treatment accessory according to a sixth embodiment of the invention.

FIG. 27 shows a treatment accessory 200 according to a sixth embodiment of the invention. Elements in this embodiment that are identical to elements in the previous embodiments are assigned the same reference numerals and the description thereof is omitted.

In this embodiment, a manipulation portion 220 is provided with an outer cylinder 221 and a manipulating shaft 222. A connecting nozzle 231 is provided to the outer cylinder 221 and the manipulating shaft 222 is formed as a solid cylinder. In this embodiment, since the connecting nozzle 231 is connected directly to the outer cylinder 221, the channel 32 through the manipulating shaft 22 of the previous embodiment is not required. Otherwise, the structure and operation of the treatment accessory 200 is the same as in the previous embodiment.

Figure 28:
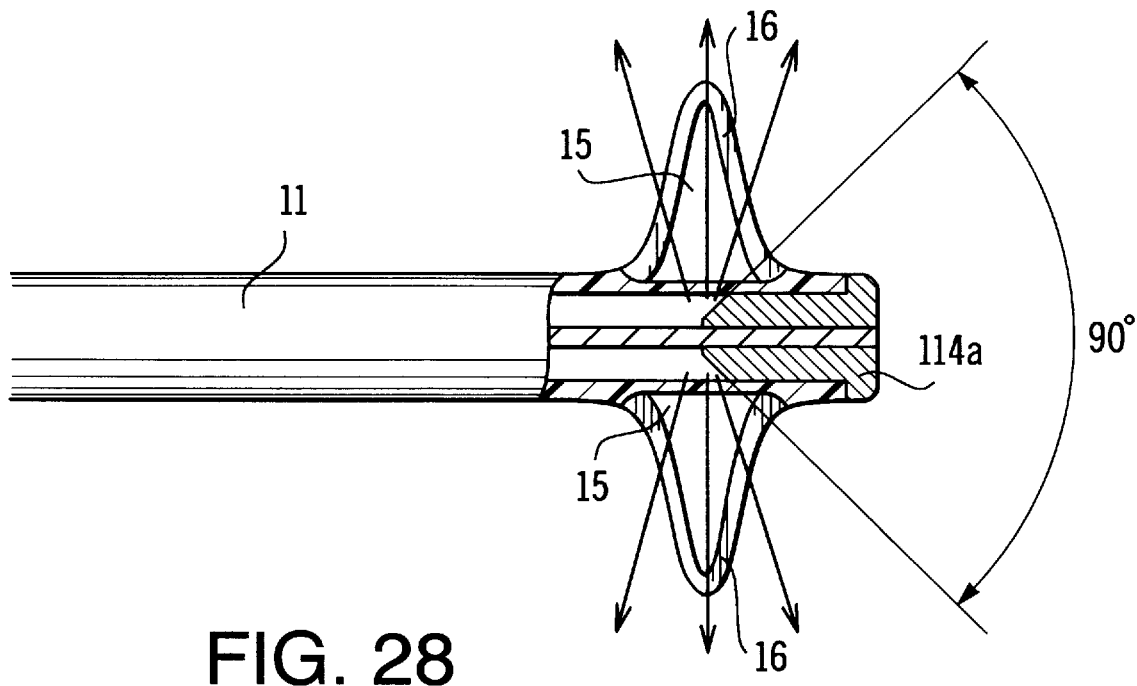
FIG. 28 is a sectional side view of the distal end portion of the treatment accessory of FIG. 19 showing an alternative tip.
Figure 29:
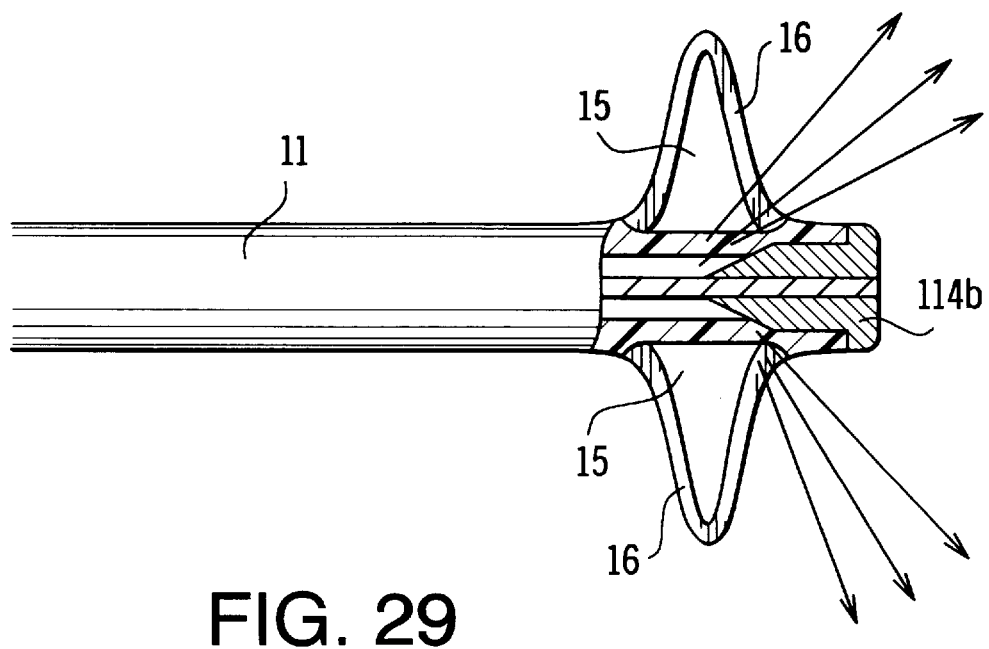
FIG. 29 is a sectional side view of the distal end portion of the treatment accessory of FIG. 19 showing another alternative tip.
Figure 30:
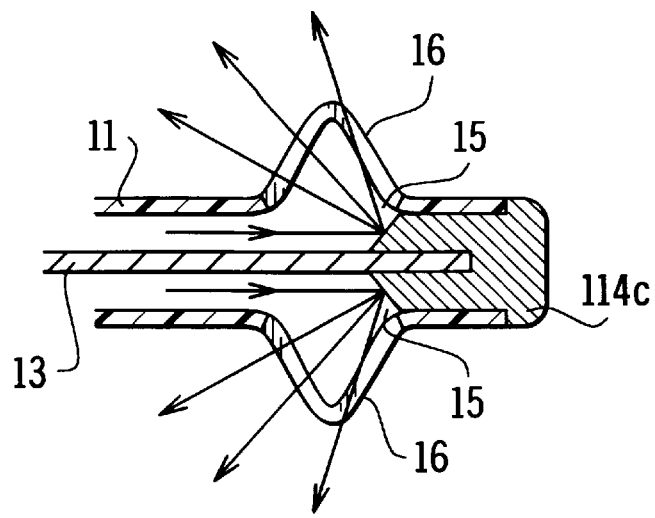
FIG. 30 is a sectional side view of the distal end portion of the treatment accessory of FIG. 19 showing yet another alternative tip.

FIGS. 28 to 30 show alternative arrangements of the tip 114 which may be used to alter the direction of ejection of solution from the flexible tube 11.

FIG. 28 shows a tip 114a which has a proximal side formed into a cone shape having an angle of 90 degrees. In this alternative, as shown by the arrows in FIG. 28, most of the solution is ejected toward the side of the flexible tube 11 at roughly right angles to the axis (i.e., laterally).

In contrast, FIG. 29 shows a tip 114b which has a proximal side formed into a cone shape that has an angle less than 90 degrees, such that the solution is ejected toward the distal end of the flexible tube 11. Further, FIG. 30 shows a tip 114c which has a proximal side formed into a cone shape that has an angle larger than 90 degrees, such that the solution is ejected away from the distal end of the flexible tube 11 (i.e. back toward the feed direction).

Thus, depending on the shape of the proximal surface of the tip 114 and the degree of openness of the slits 15, the ejection of solution can be controlled according to the requirements of the treatment accessory 100, 200.

As shown in FIG. 30, the distal end of the wire 13 need not protrude further than the tip 14.

Figure 31:
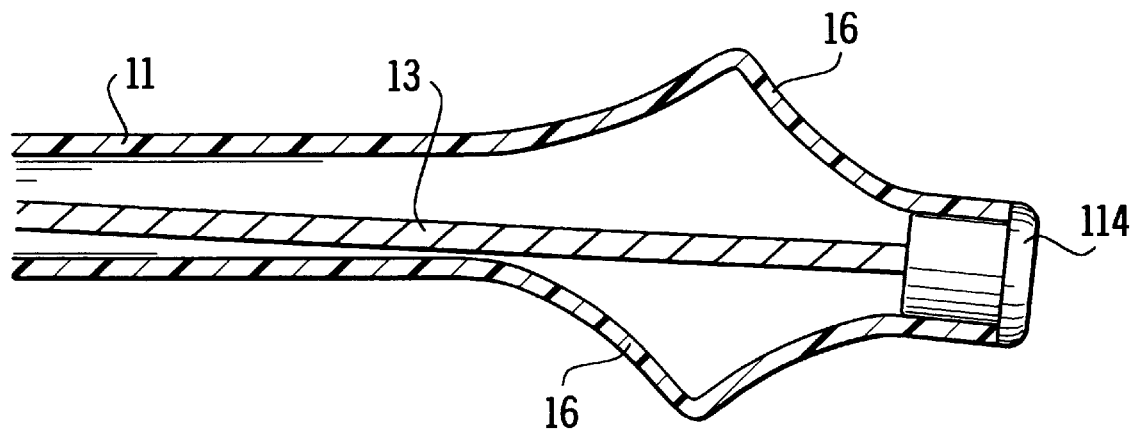
FIG. 31 is a sectional side view of the distal end portion of the treatment accessory of FIG. 19 illustrating twisting of a flexible tube.
Figure 32:
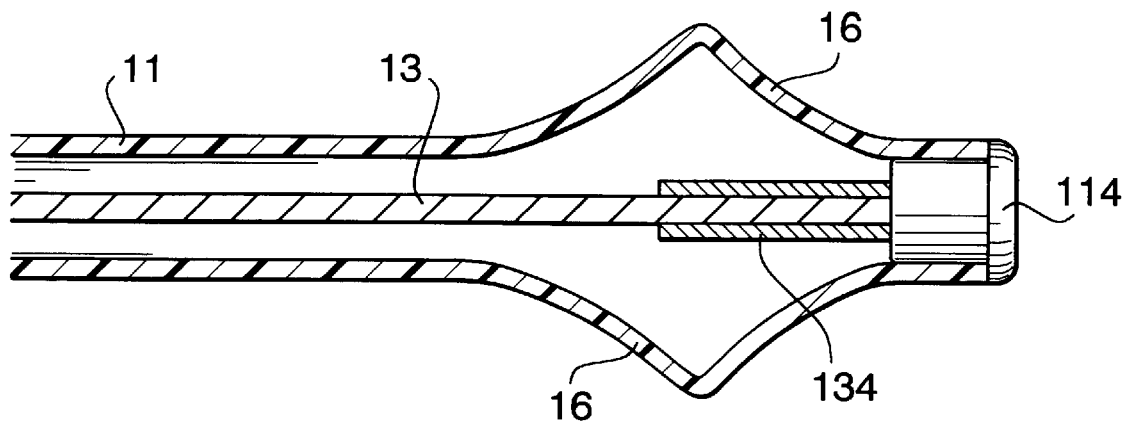
FIG. 32 is a sectional side view of the distal end portion of the treatment accessory of FIG. 19 illustrating an alternative arrangement of the distal end portion.
Figure 33:
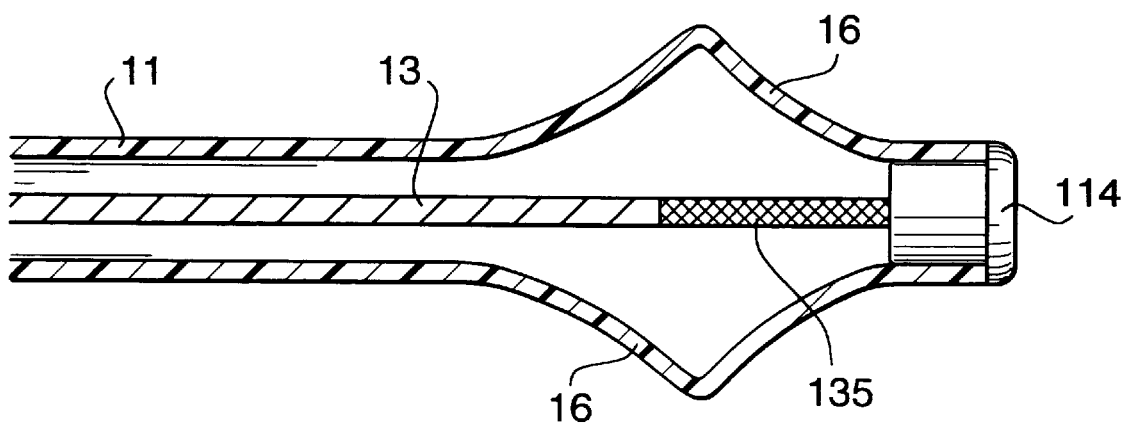
FIG. 33 is a sectional side view of the distal end portion of the treatment accessory of FIG. 19 illustrating another alternative arrangement of the distal end portion.

It is noted that, in the fifth and sixth embodiments, since the tip 114 is shorter than the tip 14 of the first and second embodiments, there is a larger chance that, if, for example, the distal end of the wire 13 is too flexible, then as shown in FIG. 31, applying a force to the wire 13 may result in bending of the wire 13 and the distal end portion of the flexible tube 11 away from the axis of the other portion of the flexible tube 11. In this case, as shown by the examples in FIGS. 32 and 33, a predetermined portion of the distal end of the wire 13 may be covered with a pipe 134 (FIG. 32) or a coating 135 of soldering or the like (FIG. 33) to prevent twisting of the distal end portion of the flexible tube 11.

It is further noted that the structure of the distal end portion of the flexible tube 11 (in particular, as described in the second, fifth, and sixth embodiments) may be useful for other purposes. For example, the flexible tube 11 may be used to collect particles from inside a body cavity. In this case, the flexible tube 11 is inserted into the body cavity, and the wire 13 is set to cause large expansion of the band sections 16.

Then, the flexible tube 11 is moved such that a particle P enters one of the slits 15, as shown in FIG. 34, then the wire 13 is pushed toward the distal end to reduce the expansion of the band sections 16.

Thus, as shown in FIG. 35 (which is a cross-sectional view along line XXXV—XXXV of FIG. 34), the particle P is sandwiched and held between two adjacent band sections 16 and the wire 13.

In particular, since the band sections 16 have an arc-shaped cross-section, they are pressed inwardly against the particle P over a wide area to securely capture the particle P. The particle P can then be removed by pulling the treatment accessory 70, 100, 200 out of the endoscope 1 or by pulling the endoscope 1 out of the body cavity.

Further, if an aspiration apparatus (not shown) is connected to the connection mouthpiece 24 or the connecting nozzle 31, particles P may be more easily drawn into the slits 15, and will not slip away, such that additional particles P may be captured before closing the slits 15 to securely hold a plurality of particles P, as shown in FIG. 36, for collection.

FIGS. 37 and 37A show a treatment accessory 300, and a groove formed thereon, according to a seventh embodiment of the invention. Again, elements in this embodiment that are identical to elements in the previous embodiments are assigned the same reference numerals and the description thereof is omitted.

In this embodiment, the treatment accessory 300 is arranged such that as well as performing either aspiration or dispensing of liquid or the like, the treatment accessory 300 may be used to perform an operation such as cauterizing an affected area inside a body cavity.

The treatment accessory 300 includes a manipulating portion 320 which includes the outer cylinder 221 and a manipulating part 322. A proximal end of the flexible tube 11 is attached to the outer cylinder 221 and a distal end of the flexible tube 11 is connected to a light-transparent laser probe tip 314 through a connecting ring 312. The laser probe tip 314 is, for example, as described in Japanese Laid-Open Patent Publication No. SHO 61-181456.

A reinforced fiber optic cable 313 is fed through an entry section 322a of the manipulating part 322, through the flexible tube 11, and connects to the proximal side of the laser probe tip 314 via the connecting ring 312. The reinforced fiber optic cable 313 is formed by, for example, coating an optical fiber 313a with a protective tube or the like. The proximal end of the reinforced fiber optic cable 313 is connected to a laser generator (not shown).

Figure 38:
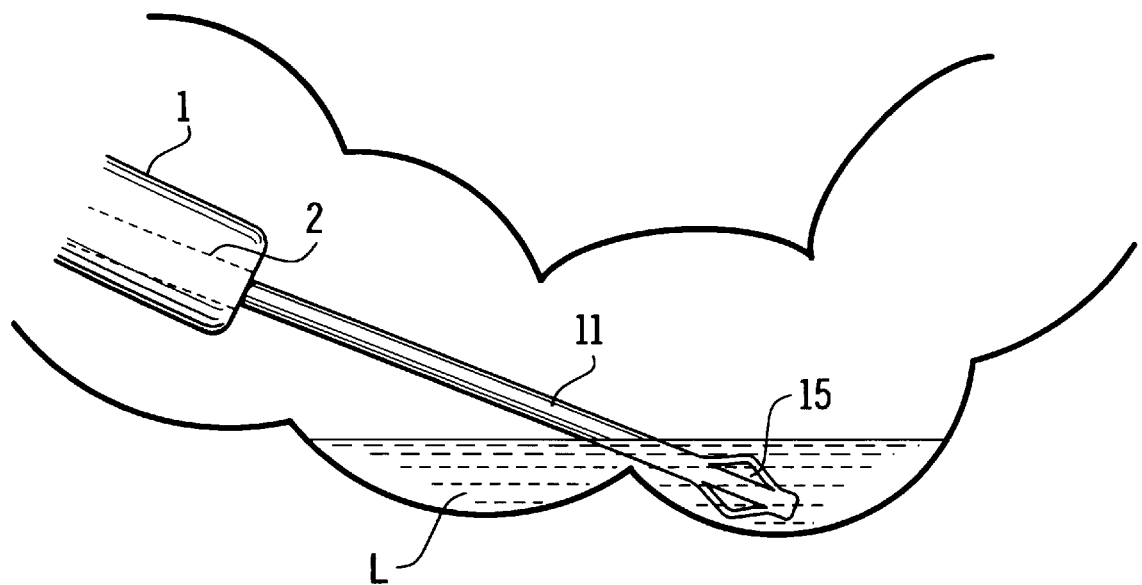
FIG. 38 is a schematic drawing showing use of the treatment accessory of FIG. 37.

With the arrangement of this embodiment, when treating an affected area, if there is a liquid L, such as blood or the like, around the affected area, as shown in FIG. 38, the distal end of the flexible tube 11 can be projected into the liquid L and the liquid L can be aspirated by attaching an aspirating apparatus (not shown) to the connecting nozzle 231 and opening the slits 15.

Thereafter, the laser probe tip 314 may be quickly used to irradiate the affected area with laser light provided through the optical fiber 13a to cauterize the affected area.

Alternatively, it may be necessary to clean away blood adhering in the proximity of the affected area to allow better observation or treatment of the affected area. In this case, a cleaning solution dispenser (not shown) may be attached to the connecting nozzle 231 and a cleaning solution can be ejected from the slits 15 to clean the surroundings of the affected area.

Figure 39:
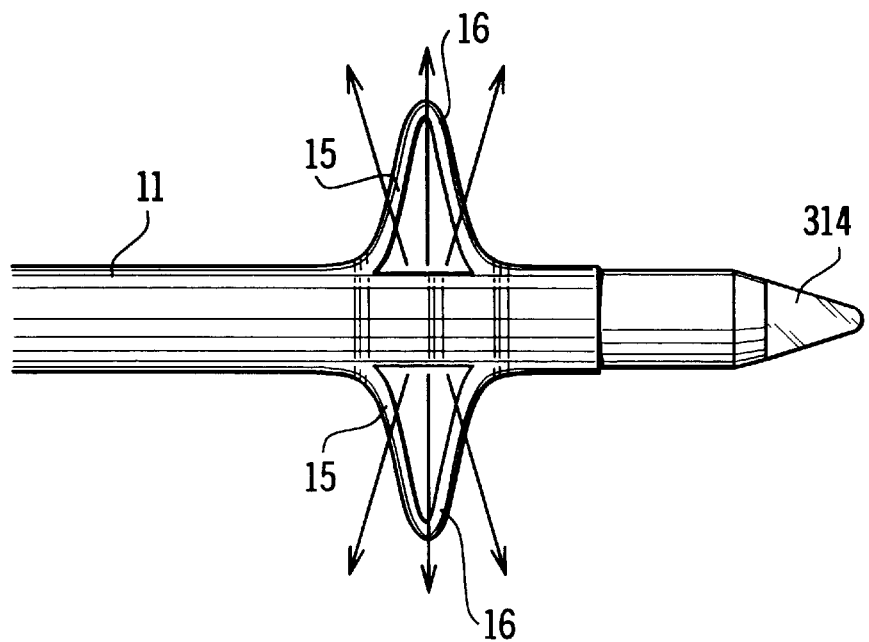
FIG. 39 is a side view of the distal end portion of the treatment accessory of FIG. 37 illustrating a lateral dispensing operation.

Further, as described above, for cleaning, the pin 128 is interlocked with the rearmost protrusion 129 so that the force exerted by the fiber cable 313 on the distal end of the flexible tube 11 reaches a maximum, and the band sections 16 are anchored at a maximum expanded state, such that, as shown in FIG. 39, since the length of the openings of the slits 15 in the axial line direction becomes shorter, the cleaning solution is forced out almost laterally to allow cleaning of a specific site at the side of the flexible tube 11. Still further, by changing the degree of expansion of the band sections 16, it is possible to freely adjust the width of the cleaning range.

Figure 40:
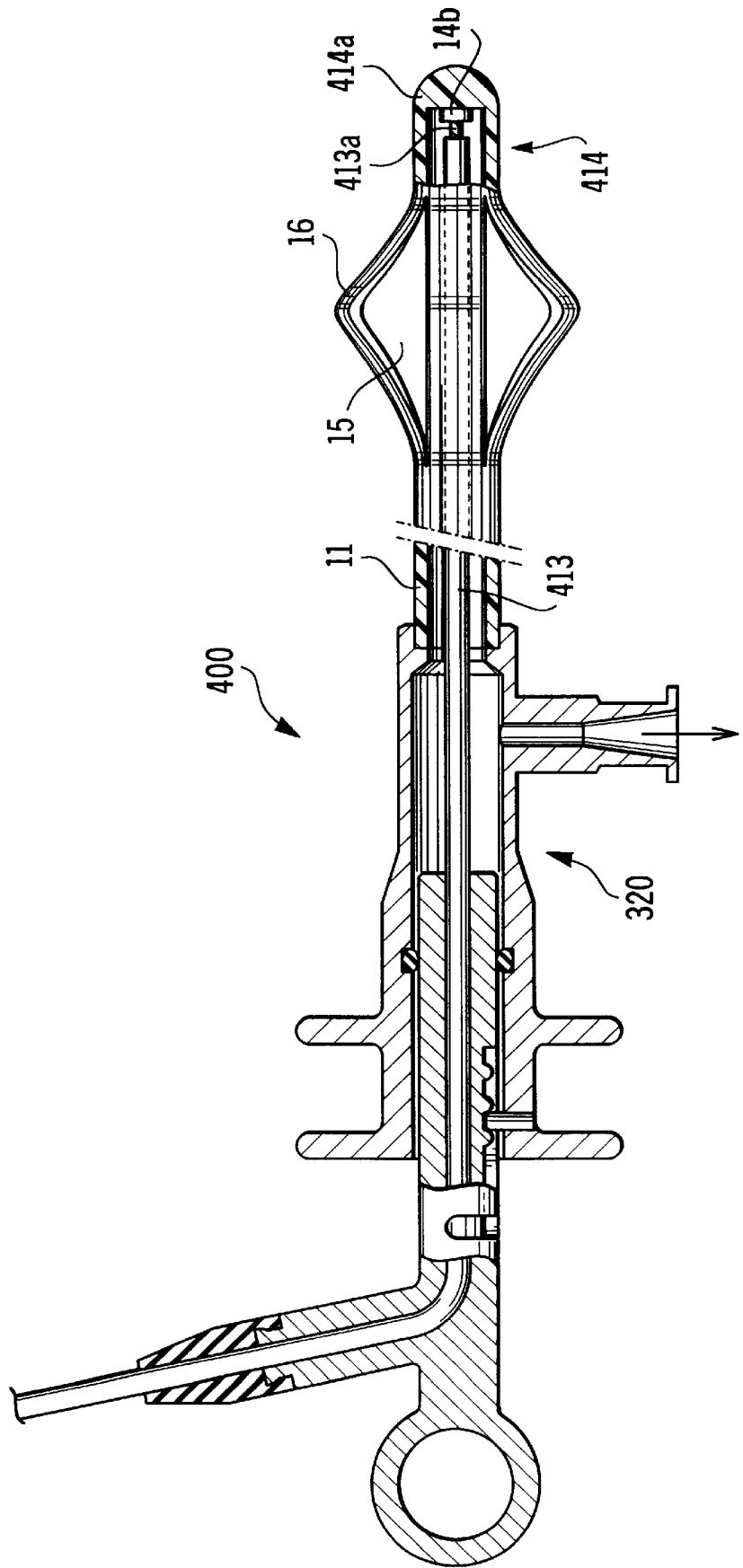
FIG. 40 is a sectional side view of a treatment accessory according to an eighth embodiment of the invention.

FIG. 40 shows a treatment accessory 400 according to an eighth embodiment of the invention. The treatment accessory 400 is provided with a heat probe tip 414 for heat cauterization that is mounted at the distal end of the flexible tube 11.

The heat probe tip 414 is, for example, as described in Japanese Patent Publication No. HEI-2-4293 and includes a heating element 414b situated in a heat-conducting cap 414a.

In this embodiment, a conducting wire 413a in a coaxial cable 413 is connected to the heating element 414b to supply electricity. The coaxial cable 413 is provided in place of the reinforced fiber optic cable 313 of the previous embodiment. Otherwise, the construction and operation is similar to the previous embodiment.

Figures 41, 41A:
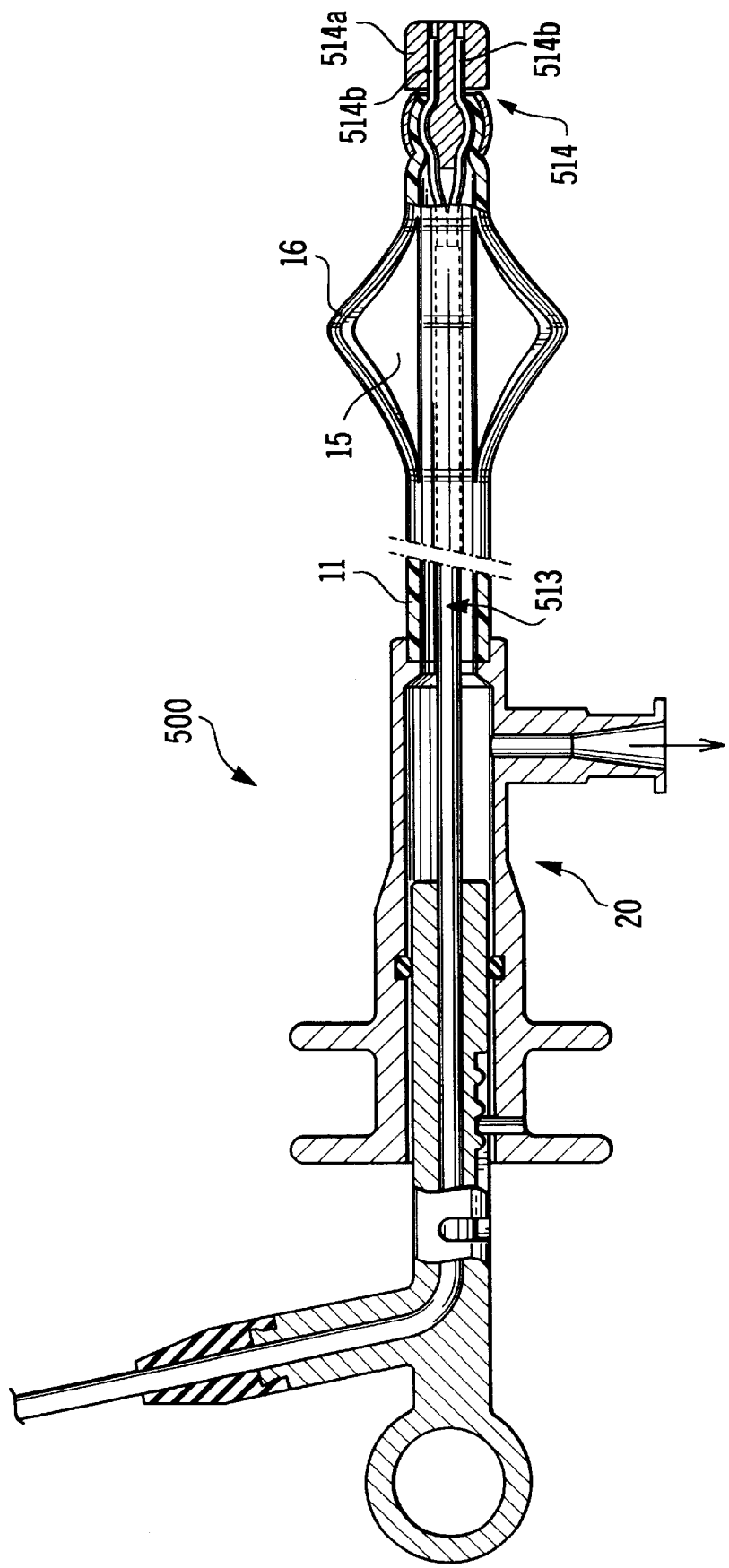
FIG. 41 is a sectional side view of a treatment accessory according to a ninth embodiment of the invention.
FIG. 41A shows a groove formed on the treatment accessory shown in FIG. 41.

FIGS. 41 and 41A show a treatment accessory 500, and a groove formed thereon, according to a ninth embodiment of the invention, wherein a lithotriptic probe tip 514 for breaking up calculi or the like by electric discharge is mounted at the distal end of the flexible tube 11.

The lithotriptic probe tip 514 is, for example, as described in Japanese Laid-Open Patent Publication No. SHO-61-181452, and includes a pair of discharge electrodes 514b situated in an electrically insulated end piece 514a.

In this embodiment, an electricity supply wire 513 is provided in place of the reinforced fiber optic cable 313 of the third embodiment and is connected to the discharge electrodes 514b. Otherwise, the construction and operation is similar to the seventh embodiment.

As described above, there is provide an improved accessory for an endoscope which has a simple structure and which is less likely to clog during aspiration. Further, a treatment accessory having a simple structure and which, if clogged, can be operated to remove the clogging without removal from the endoscope is provided.

Furthermore, there is provided an accessory for an endoscope which has a simple structure and which can be used to efficiently collect particles from inside a body cavity.

Further, there is provided an accessory for an endoscope which has a simple structure but which can be used for a variety of purposes, such purposes including dispensing liquids such as cleaning liquids and dyes, aspirating liquids and other materials, collecting particles, and cauterization of affected areas.

Although the structure and operation of a treatment accessory for endoscope is described herein with respect to the preferred embodiments, many modifications and changes can be made without departing from the spirit and scope of the invention.

What is claimed is:

1. An accessory for an endoscope, comprising a tube, said tube being provided with a distal end portion, said distal end portion having a plurality of openings, said tube having a flexible portion at least at said distal end portion thereof, a plurality of slits extending along the axis of said tube and formed on said flexible portion to define bendable band sections, a mechanism applying a force in a direction where said flexible portion is compressed along the axis of said tube, said mechanism including a wire, a distal end of said wire being connected to the distal end portion of said tube, said plurality of openings being formed as said bendable band sections expand radially due to the force applied by said mechanism, and a clearance between the wire and the inner surface of the tube allowing fluid to flow through said clearance and said plurality of openings.

2. The accessory according to claim 1, further provided with a connector portion provided at a proximal end of said tube, an external device being connected with said connector portion.

3. The accessory according to claim 2, wherein said connector portion includes a mouth piece coupled to said tube, said mouth piece receiving a connecting portion of said external device.

4. The accessory according to claim 3, wherein said mouth piece is provided coaxially with said tube.

5. The accessory according to claim 3, wherein an axis of said mouth piece is substantially perpendicular to the axis of said tube.

6. The accessory according to claim 1, wherein a proximal end of said wire is secured to a second tube which is connected to said tube.

7. The accessory according to claim 6, wherein said second tube is fixed with respect to said tube, said bendable band sections being radially expanded.

8. The accessory according to claim 6, wherein said second tube is movable with respect to said tube along the axial direction of said tube, the amount of radial expansion of said bendable band sections being determined in accordance with a position of said second tube.

9. The accessory according to claim 8, wherein a manipulation member is connected to said second tube, said wire being moved along the axis of said tube as said manipulation member is operated.

10. The accessory according to claim 8, wherein said mechanism is further provided with a stopping structure for arresting said second tube at at least one predetermined position along the axis of said tube.

11. The accessory according to claim 10, wherein said predetermined position is a position where said bendable band sections expand.

12. The accessory according to claim 10, wherein said at least one predetermined position includes at least a first and a second stopping position, the amount of radial expansion of said bendable band sections when said second tube is located at said first position being greater than that when said second tube is located at said second position.

13. The accessory according to claim 12, wherein when said tube is used for injecting fluid, said second tube is positioned at said first position.

14. The accessory according to claim 12, wherein when said tube is used for dispersing pigment solution, said second tube is located at said second position.

15. The accessory according to claim 12, wherein when said tube is used for aspiration, said second tube is located at said second position.

16. The accessory according to claim 12, wherein when said tube is used as a collecting instrument, an object can be caught when said second tube is located at said first position, and wherein an object can be grasped when said second tube is located at said second position.

17. The accessory according to claim 6, wherein a distal end portion of said wire is hard to bend.

18. The accessory according to claim 17, wherein said wire is provided with a sheath at said distal end portion, said distal end portion being hard to bend due to said sheath.

19. The accessory according to claim 17, wherein said distal end portion of said wire is rigid.

20. The accessory according to claim 6, wherein an end piece is provided at the distal end portion of said tube to which a distal end of said wire is connected.

21. The accessory according to claim 20, wherein said end piece extends in the axial direction of said tube, starting from the distal end portion of said tube.

22. The accessory according to claim 20, wherein a proximal end surface of said end piece is on the proximal end side of said tube with respect to a center of said bendable band sections when said bendable band sections are expanded radially.

23. The accessory according to claim 22, wherein said proximal end surface is formed as a conical surface.

24. The accessory according to claim 23, wherein an apical angle of said conical surface is substantially 90 degrees.

25. The accessory according to claim 23, wherein an apical angel of said conical surface is less than 90 degrees.

26. The accessory according to claim 22, wherein said proximal end surface of said end piece is a plane surface which is substantially perpendicular to the axis of said tube.

27. The accessory according to claim 20, wherein a portion of said wire adjacent to said end piece is rigid.

28. The accessory according to claim 6, wherein said wire is movable along an axis thereof.

29. The accessory according to claim 1, wherein a maximum width of each of said plurality of openings is less than or equal to an inner diameter of said tube.

* * * * *